United States Patent [19]

Cloutier

[11] Patent Number: 5,320,108
[45] Date of Patent: Jun. 14, 1994

[54] DEVICE FOR SPECIFIC INHALATION CHALLENGE, METHOD OF USE AND IMPROVED GENERATOR OF PARTICLES

[75] Inventor: Yves Cloutier, Montréal, Canada

[73] Assignee: IRSST Institut de recherche en santé et en sécurité du travail du Québec, Canada

[21] Appl. No.: 789,531

[22] Filed: Nov. 8, 1991

Related U.S. Application Data

[63] Continuation of Ser. No. 359,841, May 31, 1989, abandoned.

[51] Int. Cl.$^5$ .................... A61B 5/08; A61M 15/00
[52] U.S. Cl. ........................... 128/716; 128/203.15; 128/203.25
[58] Field of Search ............... 128/716, 719, 720, 725, 128/747, 200.18, 203.15, 203.25, 201.25, 203.16, 205.26

[56] References Cited

U.S. PATENT DOCUMENTS

| | | | |
|---|---|---|---|
| 3,311,293 | 3/1967 | Moffat | 230/209 |
| 4,402,315 | 9/1983 | Tsuda et al. | 128/747 |
| 4,558,710 | 12/1985 | Eichler | 128/720 |
| 4,660,547 | 4/1987 | Kremer, Jr. | 128/200.18 |
| 4,803,977 | 2/1989 | Kremer, Jr. | 128/200.18 |

OTHER PUBLICATIONS

IRSST, Bulletin d'information interne de l'Institut de Recherche en Santéet en Sécurité du Travail, Diagnostic de l'asthme professionnel: Validation d'un nouveau systemème, vol. 1, No. 3 Nov. 25, 1988.
C. Trudeau et al. Occupational asthma caused by exposure to ash wood dust (fraximus americana), p. 322, No. 615.
Chan-Yeung M., Lam S. Occupational asthma. Am Rev Respir Dis 1986; 133:686–703.
Pauli G., Bessot J. C., Dietemann-Molard A. L'asthme professionel: investigations et principales étiologies. Bull Physiopathol Respir 1986; 22:399–425.
Chan Yeung M., Malo J. L. Occupational asthma. Chest 1987; 130–136S.
Gervais P., Rosenberg N., Occupational respiratory allergy-Epidemiologic and medicolegal aspects. In Procedings of the XII Int. Congress of Allergology and Clinical Immunology CE Reed ed CV Meeby Co. St–Louis 1986 pp. 480–485.
Raffle P. A. B., Lee W. R., McCallum R. I., Murray R. Hunter's Diseases of Occupations, 1st ed. Boston: Little, Brown and Cie, 1987, pp. 34–38.
Cockcroft D. W., Killian D. N., Mellon J. J. A., Hargreave F. E. Bronchial reactivity to inhaled histamine: a method and clinical survey. Clin Allergy 1977; 7:235–43.
Knudson R. D., Lebowitz M. D., Holberg D. J., Burrows B. Changes in the normal maximal expiratory flow-volume curve with growth and aging. Am Rev Respir Dis 1983; 127:725–34.
Malo J. L., Pineau L., Cartier A., Martin R. R. Reference values of the provocative concentrations of methacholine that cause 6% and 20% changes in forced expiratory volume in one second in a normal population. Am Rev Respir Dis 1983; 128:8–11.
Dehaut P., Rachiele A., Martin R. R., Malo J. L., Histamine dose-response curves in asthma: reproducibility and sensitivity of different indices to asses response. Thorax 1983; 38:516–22.
De Luca S., Cair N., Cloutier Y., Cartier A., Ghezzo H., Malo J. L., Acute exposure to sawdust does not alter airway caliber and responsiveness to histamine in asthmatic subjects. Eur Respir J 1988; 1:540–6.

(List continued on next page.)

Primary Examiner—Randall L. Green
Assistant Examiner—R. M. Reichle
Attorney, Agent, or Firm—Bacon & Thomas

[57] ABSTRACT

The present invention relates to a device for specific inhalation challenges, especially bronchical provocation tests, including a compressed air supply, a particle generator an exposure room, an orofacial mask, a gas-aerosol photometer, a manometer, a valve and a suction pump. The invention also relates to a method of using the device and to an improved particle generator.

21 Claims, 11 Drawing Sheets

OTHER PUBLICATIONS

Cartier A., Thomson N. C., Frith P. A., Roberts R., Hargreave F. E., Allergen-induced increase in bronchial responsiveness to histamine: relationship to the late asthmatic response and change in airway caliber. J Allergy Clin Immonol 1982; 70:170-7.

Malo J. L., Cartier A., L'Archevêque J., Ghezzo H., Martin R. R., Kinetics of the recovery from bronchial obstruction due to hyperventitation of cold air in asthmatic subjects. Eur Respir J 1988; 1:384-8.

Burge P. S., O'Brien I. M., Harries M. G., Peak flow rate records in the diagnosis of occupational asthma due to colophony. Thorax 1979; 34:308-16.

Cartier A., Pineau L., Malo J. L., Monitoring of maximum peak expiratory flow rates and histamine inhalation tests in the investigation of occupational asthma. Clin Allergy 1984; 14:193-6.

Pepys J., Hutchcroft B. J., Bronchial provocation tests in etiologic diagnosis and analysis of asthma. AM Rev Respir Dis 1975; 112:829-59.

Cartier A., Malo J. L., Dolovich J., Occupational asthma in nurses handling psyllium. Clin Allergy 1987; 17:1-6.

American Conference of Governmental Industrial Hygienists. TLVs. Threshold limit values and biological exposure indices for 1986-87. Cincinnati: ACGIH, 1987.

American Thoracic Society. Standardization of spirometry. 1987 Update. Am Rev Respir Dis 1987; 136:1285-98.

Malo J. L., Cartier A., Occupational asthma caused by exposure to ash wood dust (*Fraxinus americana*).

Block G., Tse K. S., Kijek K., Chan H., Chan-Yeung M. Baker's asthma. Clinical and immunological studies. Clin Allergy 1983; 13:359-70.

Annals of Allergy, p. 378, No. 608 evolution of Bronchial Reactivity in isocyanate-induced asthma N. Rosenberg et al.

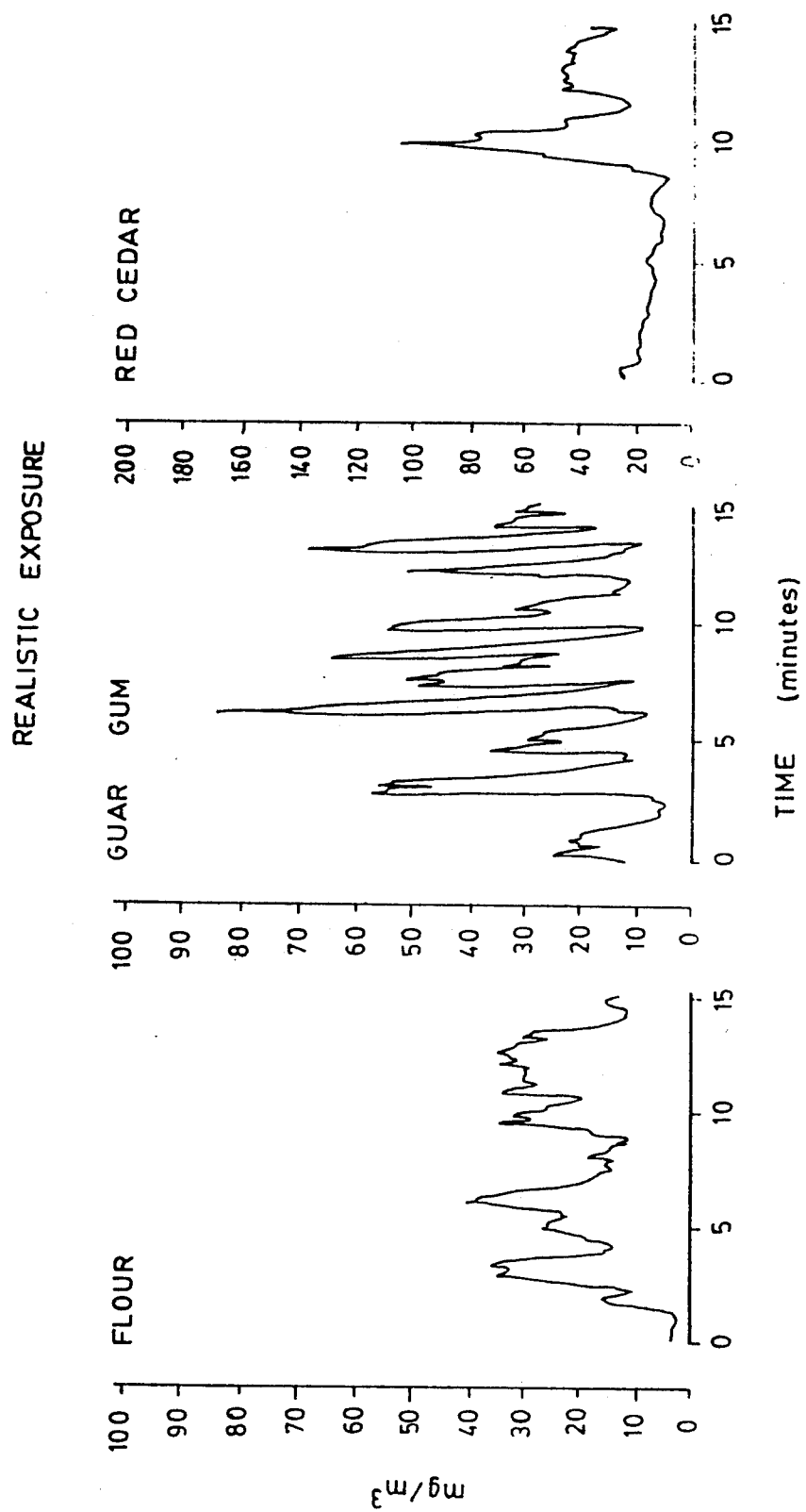

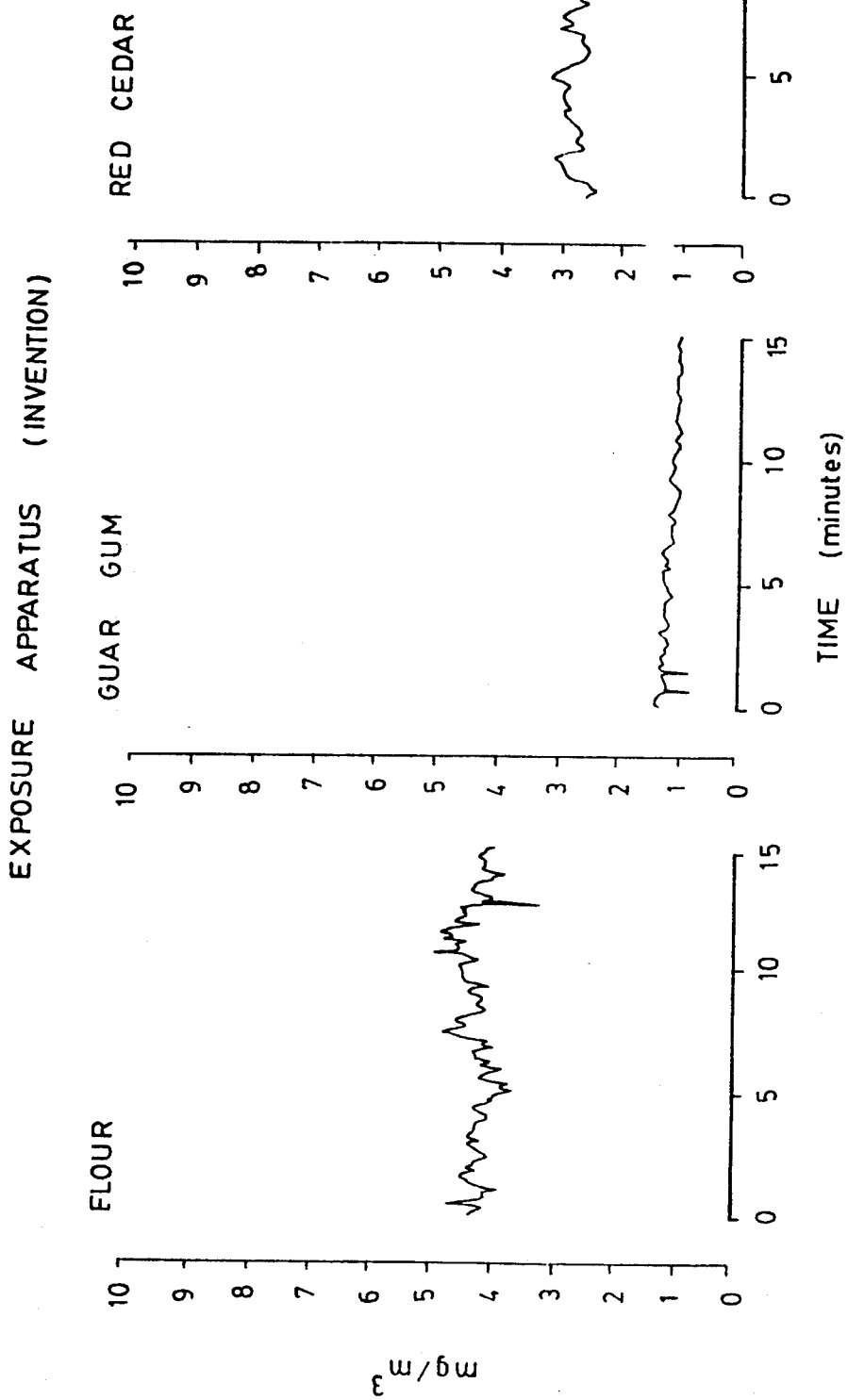

DEVICE FOR SPECIFIC INHALATION CHALLENGE, METHOD OF USE AND IMPROVED GENERATOR OF PARTICLES

This application is a continuation of application Ser. No. 07/359,841, filed May 31, 1989, now abandoned.

BACKGROUND OF TUE INVENTION

1. Field of the Invention

The present invention relates to a device for specific inhalation challenges, especially bronchial provocation tests, and to its method of use. The invention also relates to an improved generator of aerosol particles for use within the field of this invention.

2. Brief Description of the Prior Art

Occupational asthma is a common respiratory ailment. The diagnosis involves a combination of tools. Questionnaires were once the only means of diagnosis available. They were used to obtain an original description of occupational asthma among grain handlers by Ramazzini in 1700 (Raffle PAB, Lee WR, McCallum R1, Murray R. Hunter's Diseases of Occupations. 1st ed. Boston: Little, Brown and Cie, 1987, p 34–8), and among isocyanate workers, isocyanates being currently the most common causal agent. The presence of asthma can be confirmed by assessing spirometry and/or non-specific bronchial responsiveness. Immunological tests (skin tests, specific antibody tests) can confirm that there is sensitization to some agents, although they do not prove that the sensitization results in asthma. More recently serial monitoring of peak expiratory flow rates and bronchial responsiveness have been proposed for the diagnosis of occupational asthma.

Specific inhalation challenges carried out in the laboratory are still regarded as the gold standard for confirming the relationship between exposure to the suspected agent and the onset of asthma. In this experimental approach subjects are first exposed to a control product and, subsequently, to the occupational agent, in a controlled way. This procedure was first proposed by Pepys (Pepys J., Hutchcroft BJ., Bronchial provocation tests in etiologic diagnosis and analysis of asthma. Am Rev Respir Dis 1975; 112:829-59) and many new causes of occupational asthma have been identified using this method. For suspected agents available in powder form, subjects are asked to tip the product from one tray to another in a challenge room. There are several pitfalls to this procedure:

1. Subjects may be exposed to high concentrations of particles, resulting in unduly severe episodes of bronchoconstriction (Cartier A, Malo JL, Dolovich J. Occupational asthma in nurses handling psyllium. Clin Allergy 1987; 17:1-6). The concentration of particles may be higher than the standard, TLV-STEL (threshold limit value-short term exposure level), the concentration to which workers can be exposed continuously for short periods of time without suffering toxic effects. This may result in non-specific irritant reactions.

2. Exposure is erratic; the subject is exposed to high concentrations at times and acceptable levels at other times.

3. It is difficult to draw a proper dose-response curve since the concentration of particles cannot be precisely determined.

SUMMARY OF THE INVENTION

A first object of the invention is to provide a device for specific inhalation challenges, especially bronchial provocation tests, which overcomes the aforesaid drawbacks. More particularly, the object of the invention is to provide a device capable of generating inside an exposure room, a flow of an aerosol of determined composition and concentration. Advantageously, when the aerosol is inhaled by a patient, this device can continuously monitor the concentration of particles in the aerosol in order to eventually draw a proper dose-response curve, and eventually know the size of particles of this aerosol.

Another object of the invention is to provide a device that is safe for a patient having to be subjected to a specific inhalation test, especially in order to determine whether or not he suffers from occupational asthma.

A further object of the invention is to provide a device of the above type, that is easy to clean.

A further object of the invention is to provide a device that can be used for a great diversity of powders or dusts.

A further object of the invention is to provide a method for the diagnosis of occupational asthma involving the use of the aforesaid device.

A further object of the invention is to provide an improved generator of particles that is easier to use than existing generators.

The device according to the invention as claimed hereinafter includes the following structural elements:

means for continuously suspending in a flow of compressed air a determined amount of specific particles to generate a compressed aerosol of determined composition. These means (e.g. a venturi) include an inlet connected to a supply of compressed air with a tubing having opposite ends, means that are adapted to cooperate with a supply of specific particles and continuously and uniformly mix a part of said particles with the compressed air, and an outlet where the aerosol is flowing, means for adjusting the pressure of aerosol in the exposure room to a pressure close to the atmospheric pressure. These means include:

a suction pump which comprises at least one inlet, a manometer which comprises at least one inlet, an exposure room which has at least one lateral wall and opposite ends, each end being closed by an appropriate cover, said room being further provided with:

an inlet which is positioned in one of said cover and is provided with means to put it into fluid communication with the outlet of the means that generate the compressed aerosol, a first outlet which is positioned in the other cover and is provided with means to put it into fluid communication with the inlet of the suction pump, these means including a valve to adjust the draft of the pump, a second outlet which is positioned in the lateral wall of the room and is provided with means to put it into fluid communication with the inlet of the manometer, a third and a fourth outlet positioned opposite to each other in the lateral wall of the room, an orofacial mask which is adapted to cover the natural apertures of the respiratory system of a subject. This mask is provided with means to put it into fluid communication with the third outlet of the room, a device provided with an inlet, with means to put the inlet into fluid communication with the fourth outlet of the room and means to continuously draw a small part of the aerosol flowing in the room and measure its particles content (e.g. a photometer, an APS 33 AERODYNAMIC PARTICLE SIZER ® sold by TSI, Inc., a digital dust indicator (sold by Sibata) or a portable continuous aerosol monitor, model TX, PCAM-TX (sold by PPM, Inc., Knoxville)). When a photometer is used, it can be also connected to a digital reader and/or a graphic recorder and/or an integrator.

Advantageously, the exposure room consists of a tube having opposite ends and a lateral wall of cylindrical surface. This room is provided at each of its end, with:

a cover of such a diameter that it fits against the end of the tube, an "O" ring seal of such a diameter that it can be positioned between the end of the tube and the cover, fastening means adapted to hold the cover against the end of the tube and collapse the "O" ring.

Also, this room is provided with:

an inlet positioned in one of said cover, the inlet being defined by a connecting sleeve passing through the cover and making an integral part of this cover, the sleeve being connected with the outlet of the generator of particles by a tubing.

a first outlet positioned in the other cover, the outlet being defined by a first connecting sleeve passing through the cover and making an integral part of this cover, the first sleeve being connected with the inlet of the suction pump by a tubing which is provided with a valve.

a second outlet positioned in the lateral wall of the room, the outlet being defined by a second connecting sleeve passing through the wall and making an integral part of this wall, this second sleeve being connected with a branch of the manometer by a tubing.

third and fourth outlets positioned opposite to each other in the lateral wall of the room, each of these outlets being defined by a third and fourth connecting sleeve passing through the wall and making an integral part of said wall, the third sleeve of the third outlet being connected with a sleeve defining the inlet of an orofacial mask which is adapted to cover the natural apertures of the respiratory system of a subject, while the fourth sleeve of the fourth outlet is connected with a connecting sleeve defining the inlet of a device adapted to draw a small part of the aerosol flowing in the room and measure its particles content, by a tubing.

Advantageously, a device adapted to measure the size of particles of the aerosol (e.g. a cascade impactor) is further provided. To do so, a fifth outlet is further provided in the lateral wall of the room, the fifth outlet fined by a connecting sleeve passing through said wall, making an integral part of said wall and being positioned close to the third and fourth outlets, the sleeve of the fifth outlet being connected with the inlet of a device adapted to measure the size of particles (and eventually the total concentration of particles (mg/m$^3$)). The third, fourth and fifth outlets are preferably positioned in a same plane at 120° from each other and at 90° with respect to the longitudinal axis of the exposure room.

Preferably the connecting sleeve defining the inlet of the orofacial mask comprises a unidirectional valve. Also, the mask may be further provided with an outlet which is defined by another connecting sleeve having opposite ends, one end making an integral part of the mask while the opposite end is connected with one end of a tubing having opposite ends, this opposite end being positioned far away from the subject or eventually connected to evacuation means.

Preferably, the tubing positioned between the inlet of the exposure room and the outlet of the generator of particles comprises:

a first fitting of the type provided with three openings, two of the openings being connected through the tubing while the third opening is connected with one end of another tubing having opposite ends, this other tubing having its opposite end connected to a supply of compressed air and being provided with a valve. Advantageously, this first fitting has one of its openings connected with the sleeve of the inlet of the exposure room. Furthermore, the diameter of this opening may be greater than the diameter of the other opening of this first fitting in order to minimize the possibility of "backflow" when the valve of the second supply of compressed air is open.

a second and a third fitting, each fitting being of the type provided with three openings, two of the openings of each fitting being connected through the segment of tubing that is positioned between the outlet of the generator of particles and the first fitting, while the third openings of the second and third fittings are respectively connected with one of the inlets of a manometer having two distinct inlets.

a fourth fitting of the type provided with three openings. Two of the openings are connected through a segment of tubing that is positioned between the second and third fittings, while the third opening is connected to one end of a second other tubing having opposite ends, the opposite end of this second other tubing being connected with the inlet of a suction pump, and being provided with a valve.

Advantageously, a disc of foam may be positioned inside the room between the first outlet and the second to fourth (or fifth) outlets.

Advantageously, between the third opening of the fourth fitting and the valve, a segment of the second other tubing is provided with a filter which is formed of foam positioned inside a pipe having opposite ends, said opposite ends being connected through said segment of the second other tubing.

According to another embodiment, the invention relates to an improved generator of particles of the type comprising an inlet, an outlet, a base provided with at least one post supporting a platform above the base, a turntable pivotably mounted on the base and, mounted on the platform, an air ejector and a vibrator. Advantageously, this improved generator is part of the device according to the invention.

The original turntable of the existing generator of the above mentioned type is provided with a dented rail on its top surface. This rail may be loaded with a batch of powder (e.g. 150-180 ml) and is driven into a controlled axial rotation by an electric motor. This motor is remotely controlled by a switch and a dial.

The aforesaid air ejector comprises an inlet connected to a supply of compressed air, an outlet connected at one end of a tubing having opposite ends, (the opposite end of this tubing defining the outlet of the generator) and an opening that is connected with one end of a pipe having opposite ends, the other end of this pipe defining a suction station. It should be understood that when compressed air is flowing from said inlet to said outlet, a vacuum is created in the pipe.

Optionally, a cyclone separator may be positioned through a section of the tubing where a compressed aerosol is flowing, in order to further control the size of particles of the compressed aerosol.

The vibrator is an electromechanical device that generates and provides vibration, in the original generator, to the turntable in order to facilitate a stable generation of aerosol. This vibrator can be one having a frequency of about 50 or 60 Hz.

The improvements made in accordance with the invention to this known generator of particles are as follows:

1. The dented rail of the turntable is replaced by a groove which is concentrical with the axis of rotation of the turntable. This groove has a bottom having a smooth surface and lateral walls having smooth surfaces that diverge from each other from the bottom of the groove to the top surface of the turntable.

2. A hopper is mounted on the platform. This hopper is intended to contain a batch of specific particles in powder forms, and includes the following elements:

a reservoir which is intended to contain a sufficient amount (or batch) of particles and has an open (or closed) top, a bottom, lateral walls that converge to each other from the top to the bottom and an opening positioned in at least one lateral wall in the vicinity of said bottom. This opening defines a discharging station for the particles.

an endless screw passing through the opening and being at least housed in part inside the reservoir and contacting the particles, means adapted to be mechanically connected to said screw and to drive it in an appropriate and controlled axial rotation to continuously and uniformly discharge particles through the opening of the reservoir. These means may include an electric stepping motor whose shaft is mechanically connected (preferably axially connected) with one end of the screw. This electric stepping motor is advantageously remotely controlled by a power supply comprising a switch and a dial.

In the aforesaid improvements, it should be understood that:

distinct segments of the groove are respectively positioned under the opening of the reservoir (discharging station) and said other end of the pipe of the air ejector (suction station);

the vibrator provides vibration to the reservoir to continuously bring the particles into a full contact with the part of the screw that is housed inside the reservoir; and when particles are discharged, they fall uniformly and continuously from the opening of the reservoir (discharging station) into the groove which uniformly and continuously convey them toward the end of the pipe of the air ejector (suction station) where they are uniformly and continuously aspirated by the vacuum and mixed with the flow of compressed air.

According to another embodiment, the invention relates to a method for carrying out specific inhalation challenges with the aforesaid device. More particularly, the following steps are carried out:

the valve positioned between the suction pump and the first outlet of the exposure room is fully open, the suction pump is started;

the device for continuously measuring the particles content of the aerosol is started;

a flow of compressed air is established through means for continuously generating a compressed aerosol of determined composition, from the supply of compressed air toward the outlet of said means;

means for continuously and uniformly mixing specific particles with the compressed air are started and a flow of aerosol is established through the exposure room;

the valve positioned between the first outlet of the exposure room and the suction pump is partly closed until the pressure inside the exposure room which is read on the manometer is close to (preferably slightly lower than) the atmospheric pressure;

a subject covers the natural apertures of his respiratory system with the orofacial mask and breathes at least one time a part of the aerosol that is flowing in the exposure room while the device is continuously measuring the particle content of said aerosol. Advantageously when a subject breathes more than one time, a chronometer can be used in order to measure the exposure time.

More particularly, the invention relates to a preferred method for carrying out specific inhalation challenges with a device of the type including:

A) means for continuously generating a flow of compressed aerosol of determined composition and including a generator of particles of the type comprising an inlet, an outlet, a base provided with at least one post supporting a platform above said base, a turntable pivotably mounted on the base and which can be driven into a controlled axial rotation by an electric motor, and, mounted on the platform, an air ejector, a hopper and a vibrator, and wherein:

the air ejector is of the type comprising an inlet connected to a supply of compressed air, an outlet connected at one end of a tubing having opposite ends, the opposite end of this tubing defining the outlet of the generator, and an opening that is connected with one end of a pipe having opposite ends, the other end of this pipe defining a suction post, such that when compressed air is flowing from said inlet to said outlet, a vacuum is created, in the pipe, the hopper includes:

a reservoir containing a sufficient amount of specific particles and having an opened top (or closable top), a bottom, lateral walls that converge to each other from the top toward the bottom, and one opening positioned in a lateral wall in the vicinity of the bottom, an endless screw passing through said opening and being at least in part in contact with said particles, means adapted to be mechanically connected to said screw and to drive it in an appropriate and controlled axial rotation in order to continuously and uniformly discharge particles through said opening.

The turntable is of the type comprising:

a disc having a top surface and a concentrical axis of rotation.

a groove provided in the top surface and concentrical with its axis of rotation, said groove having a smooth bottom and smooth lateral walls that diverge from each other from the bottom of said groove to the top surface of the disc.

The turntable is rotationally mounted on the base in such a way that distinct segments of the groove are respectively positioned under the opening of the reservoir and the suction station.

The vibrator includes an electromechanical device mounted on said platform and allowing to communicate vibrations to the reservoir of the hopper in order to continuously bring the particles contained in the reservoir toward its bottom and thus allow full contact between the screw or a part of the screw and the particle.

B) Means are provided for adjusting the pressure of aerosol in the exposure room to a pressure close to the atmospheric pressure. The adjusting means include:

a first suction pump which comprises at least one inlet.

a first manometer which comprises at least one inlet.

an exposure room which includes a cylindrical pipe having opposite ends and a lateral wall of cylindrical surface. The room is provided at each of its ends with:

a cover of such a diameter that it fits against the end of the pipe.

an "O" ring seal of such a diameter that it can be positioned between the end of the pipe and the cover.

fastening means adapted to hold the cover against the end of the pipe and collapse the "O" ring. This exposure room is also provided with:

an inlet positioned in one of said covers and defined by a connecting sleeve integral with and passing through the cover. The sleeve is connected with the outlet of the generator of particles by tubing, a first outlet positioned in the other cover, and defined by a connecting sleeve integral with and passing through the cover. The sleeve is connected with the inlet of the first suction pump by tubing provided with a valve, a second outlet positioned in the lateral wall of the room. The outlet is defined by a connecting sleeve passing through and integral with the wall. The sleeve is connected with a branch of the first manometer by tubing, a third, a fourth and a fifth outlet positioned close from each other in the lateral wall of the room. Each outlet is defined by a connecting sleeve passing through the wall and making an integral part of said wall. Preferably, the third, fourth and fifth outlets are positioned at 120° from each other in a plane making 90° with respect to the longitudinal axis of the exposure room. The sleeve of the third outlet is connected with a sleeve defining the inlet of an orofacial mask which is adapted to cover the natural apertures of the respiratory system of a subject. The sleeve of the fourth outlet is connected with a connecting sleeve defining the inlet of a photometer, adapted to draw a small part of the aerosol flowing in the room and measure its particles content, by tubing. The fifth outlet which is provided in the lateral wall of the room is defined by a connecting sleeve passing through and integral with the wall, and positioned close to the third and fourth outlets, the sleeve of the fifth outlet being connected with the inlet of a cascade impactor adapted to measure the size of particles, the cascade impactor being connected to a second suction pump by a tube having opposite ends, the tubing between the inlet of the exposure room and the outlet of the generator of particles includes:

a first fitting of the type provided with three openings, two of the openings being connected through the tubing while the third opening is connected with one end of another tubing having opposite ends, this other tubing having its opposite end connected to a second supply of compressed air and being provided with a valve, a second and a third fitting, each fitting being of the type provided with three openings, two of the openings being connected through the segment of tubing that is positioned between the outlet of the generator of particles and the first fitting, while the third openings of the second and third fi&tings are respectively connected with one inlet of a second manometer having two distinct inlets, a fourth fitting of the type provided with three openings, two of the openings being connected through the segment of tubing that is positioned between the second and third fittings, while the third opening is connected to one end of a second other tubing having opposite ends, the opposite end of this second other tubing being connected with the inlet of a suction pump and being provided with a valve, C) an orofacial mask which is adapted to cover the natural apertures of the respiratory system of a subject, and which is at least provided with means to put the mask into fluid communication with the third outlet of the room. The connecting sleeve defining the inlet of the orofacial mask includes a unidirectional valve, and the mask is further provided with an outlet which is defined by another connecting sleeve having opposite ends, one end making an integral part of said mask while the opposite end is connected with one end of a tubing having opposite ends, this opposite end being positioned far away from the subject or eventually connected with evacuation means.

D) a device provided with an inlet, with means to put the inlet into fluid communication with the fourth outlet of the room and means to continuously draw a small part of the aerosol flowing in the room and measure its particle content, the device including a photometer of the type designed for gas and/or aerosol, E) a device provided with an inlet, with means to put the inlet into fluid communication with the fifth outlet of the room and means to continuously draw a small part of the aerosol flowing in the room and measure the particles sizes, The device including a cascade impactor connected to a suction pump via a tube having opposite ends.

A method of carrying out this preferred embodiment is as follows:

the valve positioned between the first suction pump and the first outlet of the room is completely opened, the first, second and third suction pumps and the photometer intended to continuously draw a part of the aerosol flowing in the exposure room in order to measure its particles content are started, a flow of compressed air is established through the generator of particles, the turntable and the vibrator are started, and the screw is started and drive to a constant speed of rotation.

the valve positioned between the first suction pump and the first outlet of the room can be partly closed until the pressure read on the first, manometer is set close to the atmospheric pressure at which time the concentration of particles in the aerosol is read on the photometer. It should be understood that if the particle content of the aerosol is too high, it is possible to reopen the valve between the first suction pump and the first outlet of the exposure room and then to either open in part the valve positioned between a second supply of compressed air and the third opening of the first fitting (dilution of the compressed aerosol) and check on the first manometer whether on not the pressure is around the atmospheric pressure (preferably slightly lower than the atmospheric pressure) and check on the second manometer whether or not the aerosol is flowing in the appropriate direction; it is also possible to reopen the valve between a first suction pump and the first outlet of the exposure room and then to open in part the valve positioned between the third suction pump and the third opening of the fourth fitting (division of the compressed aerosol). The valve positioned between the first suction pump and the first outlet of the room is then adjusted until the pressure read on the first manometer is set close to the atmospheric pressure(preferably slightly lower than the atmospheric pressure), and this procedure is eventually repeated until the concentration read on the photometer corresponds to the one at which a subject has to be challenged.

then a subject covers the natural apertures of his respiratory system with the orofacial mask and breathes at least one time a part of the aerosol that is flowing in the exposure room, while the photometer is continuously and simultaneously measuring the particle content of the aerosol and the cascade impactor is sampling the aerosol in order to get the particle size distribution. When more than one breath is expected, a chronometer can be used to measure the exposure time. When a graph recorder is connected to the photometer, this recorder may replace the chronometer.

Advantageously, the pressure inside the exposure room is always set slightly below the atmospheric pressure.

Advantageously, the device is installed inside a challenge room. All the suction pumps are outside of the room (where the air could be evacuated outdoors), as is the outlet of the tubing connected to the orofacial mask.

BRIEF DESCRIPTION OF THE DRAWINGS

The invention will be better understood with reference to the following non-restrictive description of preferred embodiments thereof, taken in connection with the accompanying drawings in which:

FIGS. 7a, 7b and 7c are curves giving concentrations of particles recorded by a photometer located 10 cm from the mouth of a subject who underwent specific inhalation challenges by tipping the relevant powder from one tray to another, at times showing huge variations in concentrations with very high doses;

FIGS. 8a, 8b and 8c are curves giving the concentrations of particles recorded by the device of FIGS. 2 to 6, showing stable concentrations of three powders.

DETAILED DESCRIPTION OF THE PREFERRED EMBODIMENTS

Figure 1:
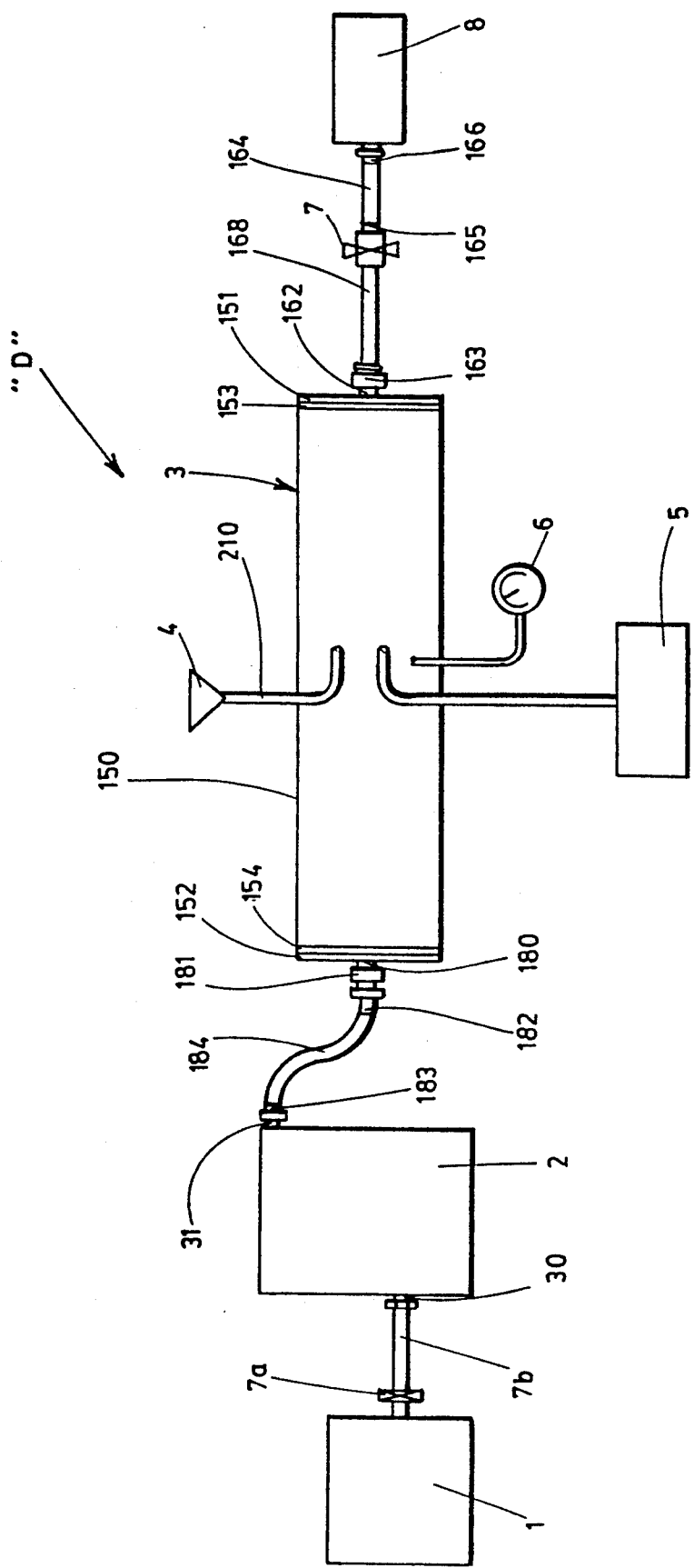
FIG. 1 is a schematic view of a device according to the invention.
Figure 2:
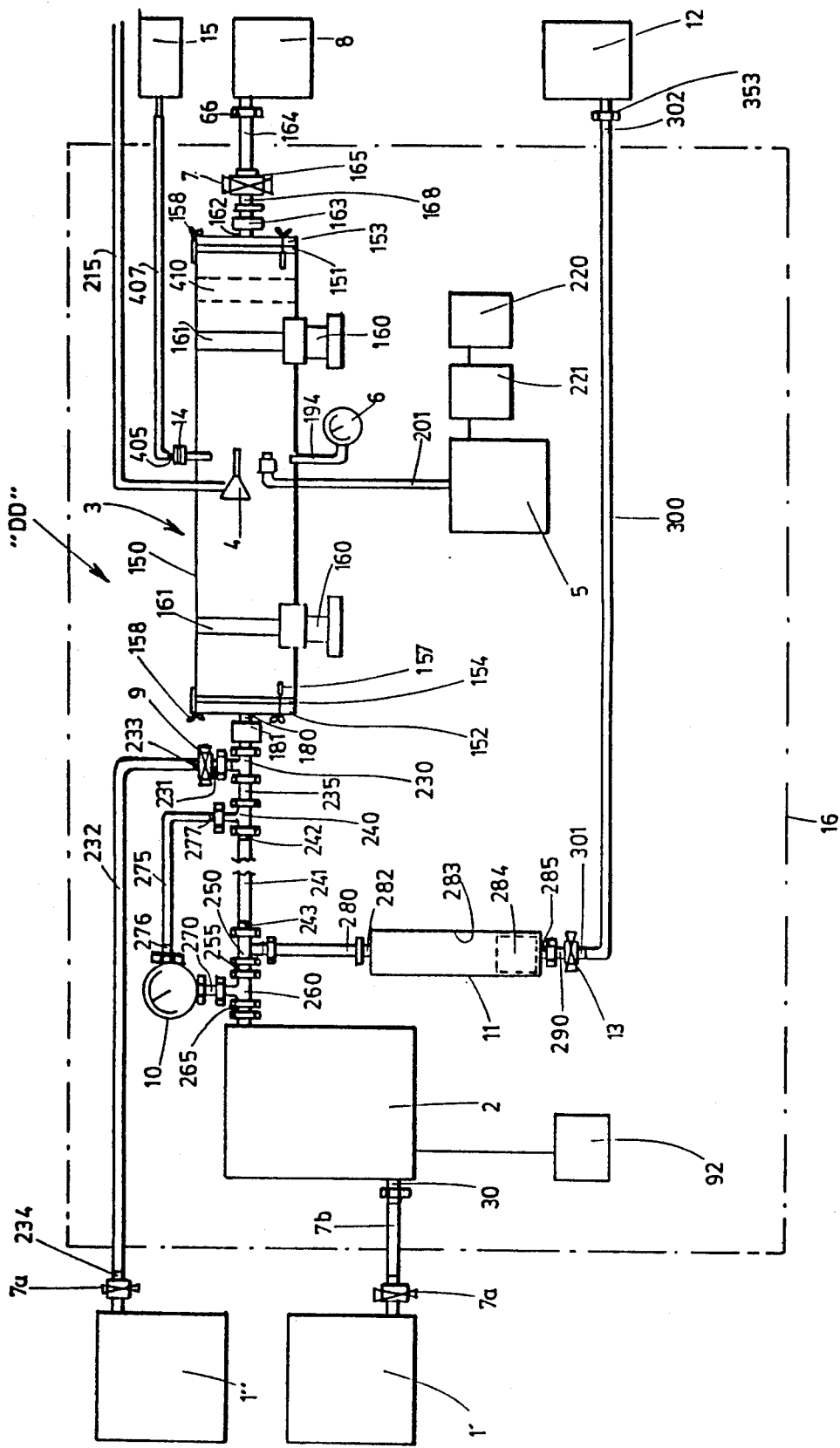
FIG. 2 is a schematic view of a particularly preferred embodiment of a device according to the invention.

In FIG. 1 of the drawings, there is represented a device "D" according to the invention. This device "D" includes a supply of compressed air 1, a generator of particles 2, an exposure room 3, an orofacial mask 4, a gas analyser or aerosol photometer 5, a manometer 6, a valve 7 and a suction pump 8.

The air supply 1 is either a supply of medicinal compressed air of the type commonly available in hospitals, or bottle(s) of medicinal compressed air. Of course, both types of aforesaid supplies are conventionally provided with one or several valves 7a.

The generator of particles 2 is the aforesaid improved version of a generator of particles sold under the trade name SIBATA MICRO FEEDER MF2. Improvements to this generator of particles also form an object of the present invention.

Figure 3:
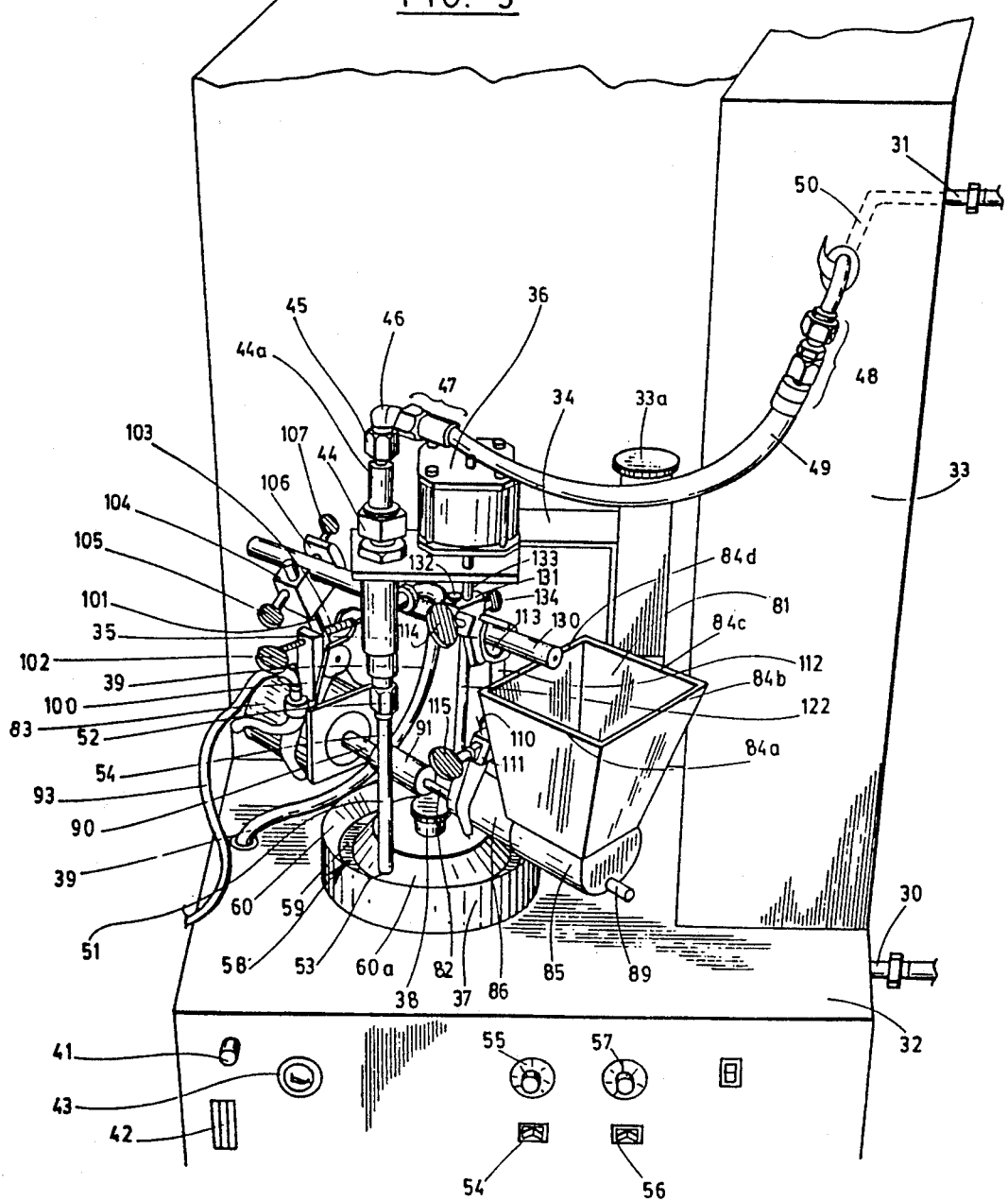
FIG. 3 is a view showing an improved generator of particles according to the invention.
Figure 4:
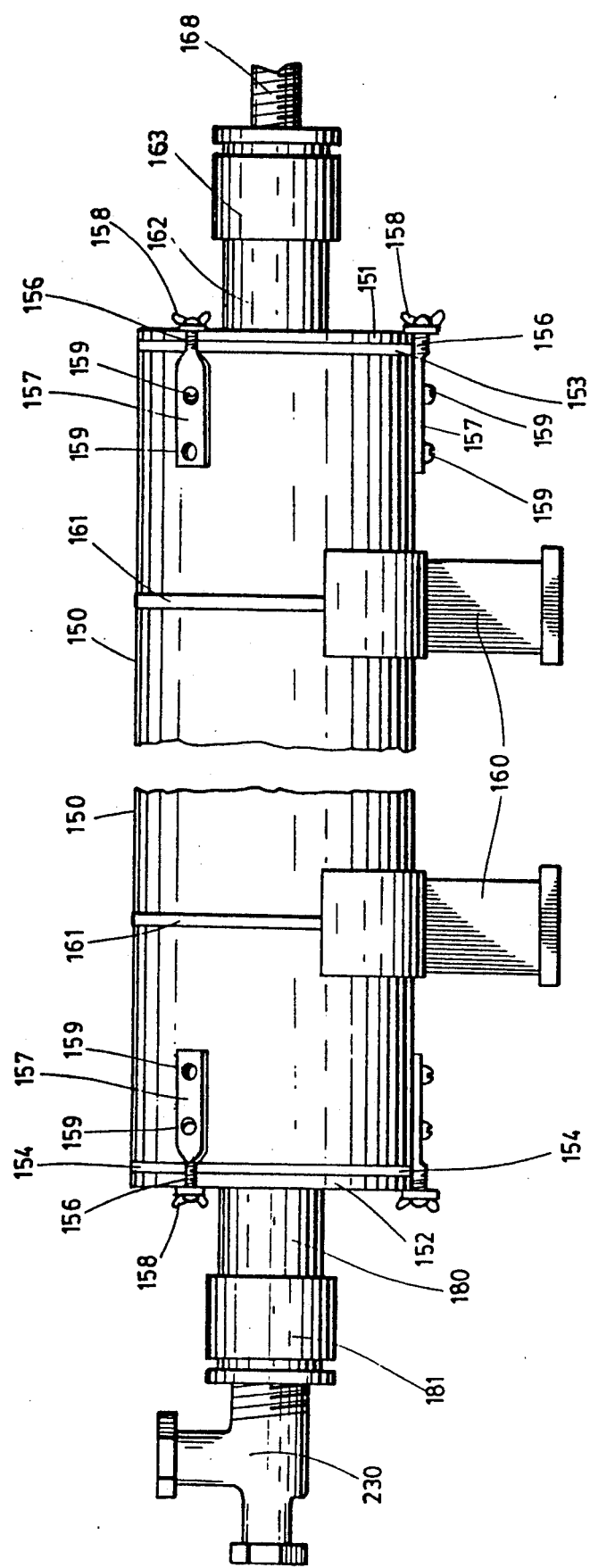
FIG. 4 is partial views of both ends of an exposure room according to the invention, respectively.

More particularly, the improved generator of particles as is shown in FIG. 3, is a modified SIBATA MICRO FEEDER MF2. This improved generator includes an inlet 30, an outlet 31, a base 32 provided with a post 33 supporting a platform 34, a turntable 37 pivotably mounted on said base 32, and, mounted on platform 34, an air ejector 35, a hopper 80 and a vibrator 36. A height adjustment means 33a is further provided between the platform 34 and the post 33.

The inlet 30 is threaded and connected to one threaded opening of a valve 7a with a hose 7b provided at each of its ends with conventional threaded brass fittings, the valve 7a having conventional threaded brass fittings. Connection between threaded portions may be made air-tight with a film of TEFLON® (trademark) therebetween.

The air ejector 35 is the one standard with the SIBATA MICRO FEEDER MF2 and it comprises an inlet, an outlet and an opening. The inlet is connected to the inlet 30 by an appropriate gas line including the hose 39, the needle valve 41, the flowmeter 42 and the pressure gauge 43, all standard with the SIBATA MICRO FEEDER MF2. The outlet of the ejector is connected with the outlet 31 by an appropriate gas line including pipe fittings 44 to 48, the hose 49 and the tubing 50. The opening of the ejector is connected to one end of a semi flexible tube 51 (e.g. an aluminum tube coated with a film of plastic material) by a fixing nut 52. The opposite end 53 of the tube 51 defines the "suction station". The semi flexible tube advantageously replaces the glass nozzle that is standard with the SIBATA MICRO FEEDER MF2.

The vibrator 36 is the one standard with the SIBATA MICRO FEEDER MF2. This vibrator which is fastened on the platform 34, is an electromechanical device sold under the trade name OMRON, provides 50 Hz and is remotely controlled by a switch 54 and a dial 55 (numbered from 0-11), all standard with the SIBATA MICRO FEEDER MF2.

The original turntable of the generator of particle SIBATA MICRO FEEDER MF2 is replaced by a turntable 37. This turntable is mounted above the base 32 at one end of a shaft 38 which is standard with the SIBATA MICRO FEEDER MF2. This shaft 38 is mechanically connected to an electric motor which is remotely controlled by a switch 56 and a dial 57 (numbered from 0-11). The electric motor, the switch 56 and the dial 57 are standard with the SIBATA MICRO FEEDER MF2. The turntable 37 is a monolithic disc which is provided with a groove 58 having a smooth bottom 59, and lateral walls 60 and 60a. The bottom 59 and lateral walls 60 and 60a have smooth surfaces. The lateral wall 60 is near the periphery of the disc. The bottom has a width slightly larger than the diameter of the end 53 of the semi flexible tube 51. The width and the depth of the groove near the top surface of the disc are each about five times the width of the bottom 59. The turntable has a diameter of about 5¼ inches and a thickness of about one third of its diameter.

The turntable 37 is provided with a central bore which is concentric with the axis of rotation of the turntable and the groove 58. This bore is, of course, designed to fit on the shaft 38 of the generator SIBATA MICRO FEEDER MF2. This is obvious for a skilled workman and does not need particular description.

The hopper 80 includes a reservoir 81, a screw 82 and an electric stepping motor 83.

The reservoir 81 has lateral walls 84a, 84b, 84c and 84d, a hemicylindrical hollow member 85 and a cylindrical member 86. Walls 84 and members 85 and 86 are made of plastics and are joined together with an appropriate glue. A bore 87 is drilled through members 85 and 86 and a bore 88 is drilled through member 86. Bores 87 and 88 communicate together. The bore 88 has a diameter of ½ inch and is essentially vertical. The bore 87 has a diameter slightly greater than ¼ inch, and is engaged by a screw 82 having a diameter of ¼ inch.

Figure 6:
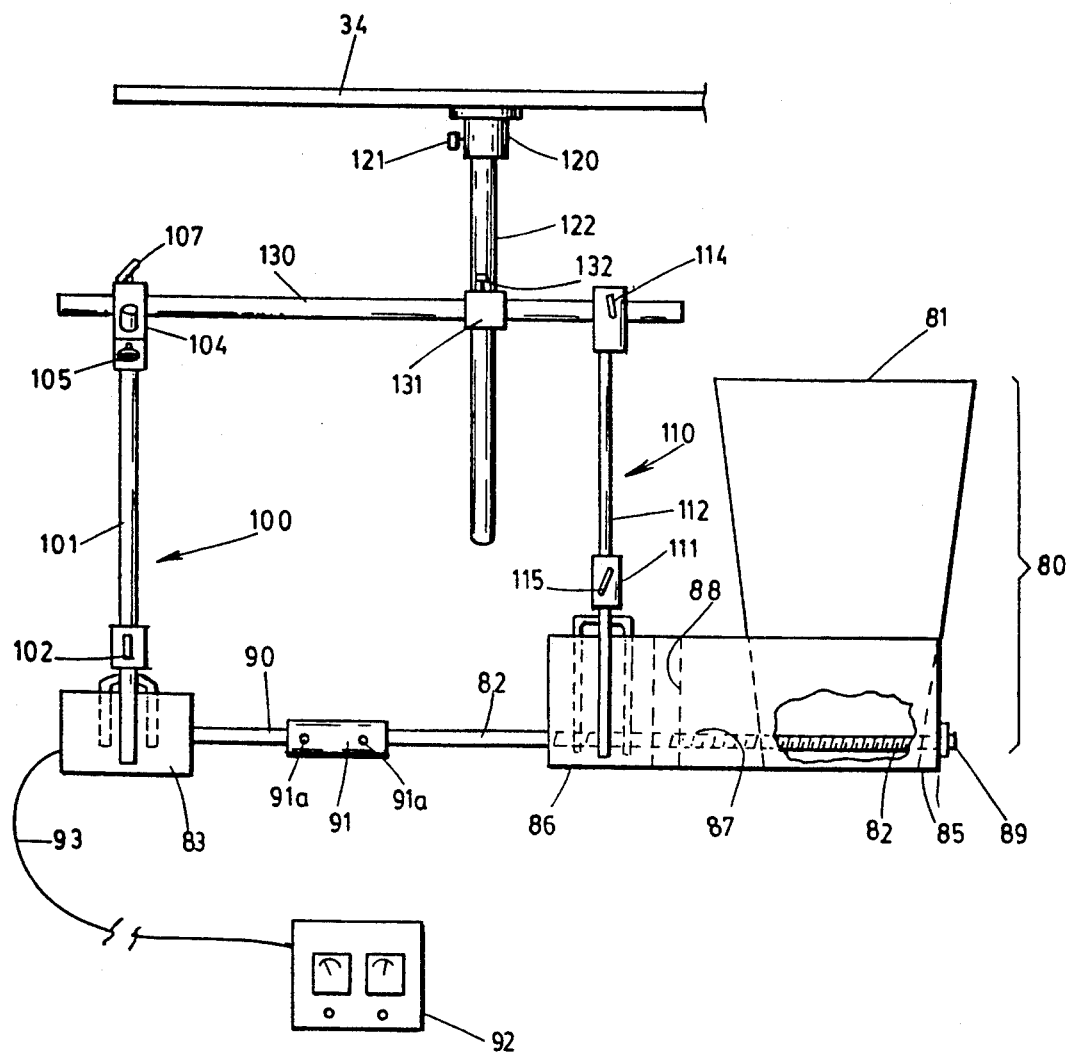
FIG. 6 shows details of the hopper not seen in FIG. 3.

The screw 82 is provided with a stopper 89 at one end thereof (outside the member 85) while the opposite end is mechanically connected to the shaft 90 of an electric stepping motor 83 with a sleeve 91. This sleeve 91 has radial locking screw 91a intended to lock the screw 82 and the shaft 90 therein. The threaded portion of the screw 82 (see FIG. 6) is at least positioned between a point located through the bore 88 and the inner surface of the member 85 near the Stopper 89.

The reservoir has a height of about 5¼ inches and a length of about 4¾ inches. Lateral walls 84b and 84d have an upper length of 3½ inches and a lower length of 1¾ inches. Lateral walls 84a and 84c have an upper width of 4¼ inches and a lower width similar to the one of walls 84b and 84d.

The stepping motor 83 (which has the following particular Series #128376, D.C. 1.65V, 4.7A, class B, Spec. BM 101025 Type M062- FC09) is remotely controlled by a switch mode laboratory power supply 92 sold under the trade name ANATEK 3000. They are connected with an electric wire 93.

The stepping motor 83 is grasped between the jaws of a common laboratory pincer 100 which is of the type having opposite jaws pivotably mounted at one end of a rod 101. These jaws are each provided with a lever and are actuated and locked against the motor 83 by screws 102 and 103. Each screw engages a corresponding threaded bore provided in a corresponding lever, and contacts the rod 101. The opposite end of the rod 101 is engaged through the bore of a laboratory rod connector 104 of the type having one bore provided with a lateral locking screw 105 and one hook 106 provided with a lateral locking screw 107.

The member 86 is grasped between the jaws of a common laboratory pincer 110 of the type having opposite jaws pivotably mounted and partly housed inside a skirt 111 which is mechanically connected to one end of a rod 112 having opposite ends. A hook 113 provided with a lateral locking screw 114 is mechanically connected at the opposite end of the rod 112. The jaws are actuated and locked against the member 86 with opposite screws 115. Each screw engages a corresponding threaded bore provided in the skirt 111 and contact a corresponding jaw.

The platform 34 of the generator SIBATA MICRO FEEDER MF2 is provided with a standard rod connector 120 provided with a bore and a lateral locking screw 121, and with a rod 122 having opposite ends, one end thereof being engaged and locked inside the bore with the screw 121.

Hooks 106 and 113 are engaged by a rod 130 and then screws 107 and 114 are tightened to thus fasten pincers 100 and 110 on rod 130. This rod is also engaged through the bore of a common laboratory connector 131 of the type having one bore provided with a lateral locking screw 132 and one hook 133 provided with a lateral locking screw 134. The rod 122 is engaged in the hook 133 and locked therein upon tightening of the screw 134, after having positioned the bore 88 slightly above the groove 58 of the turntable 37.

The exposure room 3 includes a tube 150 (e.g. plexiglass, outer diameter: 5¼ in., length: 43-7/16 in.), two covers 151 and 152 (e.g. plexiglass, diameter: 5¼ in.), two "O" rings 153 and 154 (e.g. made of resilient material, outer diameter: 5¼ in.) and six fastening means.

Figure 5:
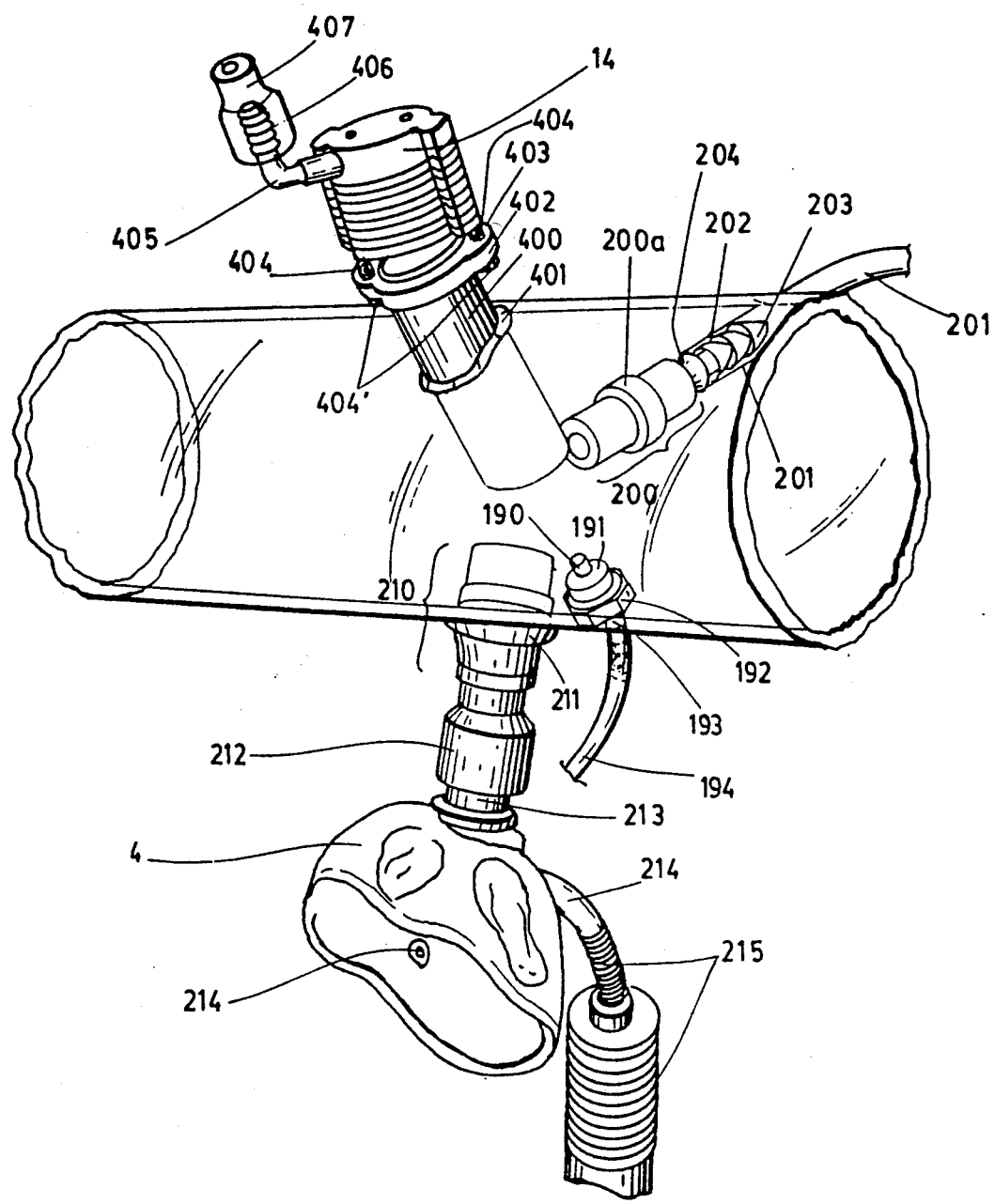
FIGS. 5a and 5b are partial views of the middle portion of an exposure room according to a particularly preferred embodiment of the invention.
Figure 5B:
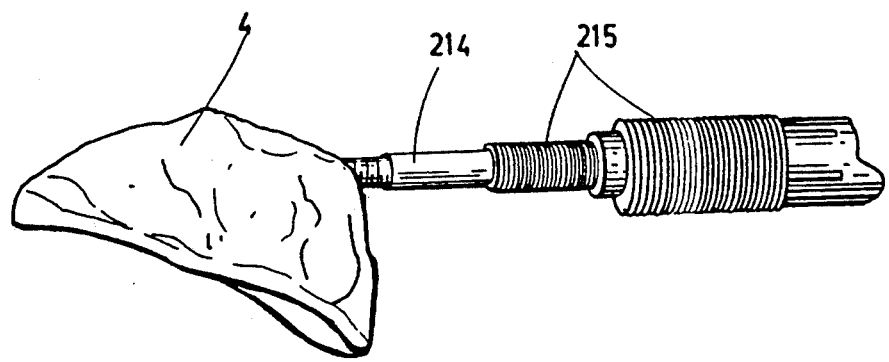
Figure 5A:
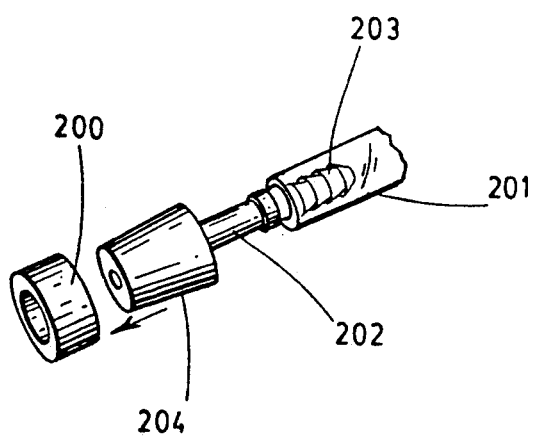

Each fastening means more particularly includes a threaded rod 156, a flat member 157 and a wing nut 158. The flat member 157 is fixed to the tube 150 with screws 159. Upon tightening of wing nuts 158, covers 151 and 152 are brought against their corresponding ends of the tube 150 and the "O" rings 153 and 154 are collapsed to thus seal the exposure room. The tube 150, a segment of which is shown in FIG. 5 do not have an outlet for sleeve 400 since there is no impactor. Optionally, covers 151 and 152 may be each provided with a peripheral shoulder where the "O" ring is supported, in which case a part of the covers is housed inside the tube 150.

The cover 151 is provided with a concentric bore in which is housed one end of an ABS sleeve 162 (outer diameter: 1¼ in.). The opposite end of this sleeve 162 is connected with one end of an ABS pipe fitting 163 (diameter: 1½ in.) of the type provided, at one end thereof, with means adapted to fit and engage tightly the opposite end of the sleeve 162, and at the other end thereof, with means adapted to fit and engage tightly the threaded end of a brass pipe 168 (diameter: ½ in.).

The junction between the cover 151 and the sleeve 162 may be sealed with a layer of silicone.

The opposite end of the pipe 168 is also threaded and screwed in a corresponding threaded bore of a valve 7 (which has two opposite threaded bores). A hose 164 is provided at each of its ends, with threaded brass fittings 165 and 166. Fitting 165 is screwed in the opposite bore of the valve 7. Fitting 166 is screwed with the corresponding threaded brass fitting of a suction pump 8. This suction pump is sold by Gast (Model 05220V103-618DX. U.S. Pat. No. 3,311,293).

The junction between the sleeve 162 and the pipe fitting 163 may be sealed with silicone. Junctions between threaded fittings and bores can be made air-tight with a film of the TEFLON ® (trademark) as is well known in the art. ABS sleeve 162, ABS fitting 163, hose 164, valve 7, brass pipe 168 and brass fittings 165 and 166 are those commonly used for gas lines and are easily assembled using steps which are very well known in the art.

The cover 152 is provided with a concentric bore in which is housed one end of an ABS sleeve 180 (outer diameter: 1¼ in.). The opposite end of this sleeve 180 is connected with one end of an ABS pipe fitting 181 (diameter: 1½ in.) of the type provided, at one end thereof, with means adapted to fit and engage tightly the opposite end of the sleeve 180, and at the other end thereof, with means adapted to fit and engage tightly the threaded end of a brass fitting 182 mounted at one end of a tubing 184. The opposite end of this tubing 184 is provided with a threaded pipe fitting 183 which is screwed on the outlet 31 of the generator 2. This outlet 31 is of course threaded.

The exposure room 3 is further provided, at its mid-length, with three bores (no optional impactor here).

In a first bore, a sleeve 190 is housed. This sleeve 190 is of the type provided with two stoppers 191 and 192 (one on each side of the wall of the tube 150) and concentrical protuberances 193. One end of a plastic hose 194 (e.g. a TYGON ® hose) is forced over the protuberances 193. The opposite end of this hose 194 is forced over the inlet of a manometer 6. This manometer (which is graded from −0.5 inch of water to 0.5 inch of water) is intended to measure the difference of pressure between the inside of the exposure room 3 and the atmospheric pressure.

In a second bore, a sleeve 200 is housed. Advantageously, the junction between the sleeve 200 and the wall of the tube 150 is sealed with a layer of silicone 200a. One end of a plastic hose 201 is forced over one end of a sleeve 202 which is provided with protuberances 203 while the other end of this sleeve 202 is forced through a bore provided in a laboratory rubber cork 204. This cork 204 is of such a diameter that it can be forced in one end of the sleeve 200 to thus tightly connect the hose 201 with the sleeve 200. The opposite end of the hose 201 is forced over the inlet of a photometer 5 (e.g. a real-time aerosol monitor, model RAM-1 sold by GCA Environmental Instruments). The RAM-1 is a portable, self-contained aerosol monitor whose sensing principle is based on the detection of near-forward scattered electromagnetic radiation in the near-infrared. This instrument uses a pulsed Ga-As semiconductor light emitting diode which generates a narrow-band emission centered on 940 nm. The scattered radiation is detected by means of a silicon photovoltaic-type diode with integral low noise preamplifier. This photometer is further provided with an analog voltage output (0–10VDC) proportional to the concentration and may be connected with a strip chart recorder and eventually to another recording device such as a digital reader and/or an integrator. This RAM-1 photometer is provided with a double diaphragm pump to produce an input flow of 2 liters/minute.

In a third bore, a sleeve 210 is housed. The junction between the sleeve 210 and the wall of the tube 150 is sealed with a layer 211 of silicone. A one-way valve 212 has one of its ends tightly forced in the sleeve 210 while its opposite end is tightly engaged by one end of a sleeve 213 whose opposite end is housed inside a bore provided in an orofacial mask 4. The one-way valve 212 is positioned so as to allow the aerosol that may be contained in the tube 150 to flow toward the mask 4. This mask 4 is also provided with another bore in which is housed a sleeve 214 including a check valve in order to prevent the surrounding air from entering the mask 4 when a subject breathes the aerosol, but allowing evacuation of the air expulsed by the subject if he has to breathe the aerosol more than one time. This kind of orofacial mask is commonly available and well known to the skilled workman.

The device of FIGS. 1, 3, 4, 5 (less the sleeve of the impactor) and 6 can be used as follows:

- the reservoir 81 is filled with a batch of specific particles of low diameter (e.g. $\leq 100$ μm advantageously $\leq 15$ μm).
- the valve 7 is completely opened and the suction pump 8 is started,
- the photometer 5 is started.
- the valve 7a is opened.
- the switch 54 is turned on and the dial 55 is set on a number selected between 0 and 11 (e.g. on the number 11). The vibrations are communicated to the hopper 80.
- the needle valve 41 is adjusted so as a pressure of about 2 kg/cm$^2$ can be read on the manometer 43 and a flow-rate of from 3 to 30 l/min can be read on the flowmeter 42,
- the valve 7 is slowly closed until the pressure read on the manometer 6 becomes close to the atmospheric pressure and preferably slightly lower than the atmospheric pressure.
- the switch 56 is turned on and the dial 57 is set on a number selected between 0 and 11 (e.g. on the number 3). Then the turntable 37 is driven into a controlled axial rotation.
- the power supply 92 is switched on and the motor 83 is started so as to drive slowly the screw 82. The speed of the screw 82 is controlled by the variation of current and/or voltage applied to the electric motor 83,
- the concentration of particles in the aerosol is read on the photometer 5 (This concentration is determined from calibration curves which are plotted according to methods well known in the art). Then, if necessary, the speed of the screw 82 may be lowered or increased so as to reach the concentration of particles at which a subject has to be challenged. Obviously the size and the thread of the screw 82 could have been changed in order to modify the concentration of particles. However, as a result, the hopper 80 might have to be changed also.
- a subject covers the natural apertures of his respiratory system with the mask 4 and inhales at least one time a part of the aerosol flowing in the exposure room 3 while the particle content of this aerosol is measured by the photometer 5, and then his reaction to the aerosol may be noted by the physician.

To stop the device "D", the power supply 92 is turned off, valves 7a and 7 are closed, the photometer 5 and the suction pump 8 are turned off, and switches 54 and 56 are turned off.

In FIG. 2 of the drawings, there is represented a particularly preferred device "DD" according to the invention. This device "DD" comprises supplies of compressed medical air 1' and 1", a generator of particles 2, an exposure room 3, an orofacial mask 4, a gas-aerosol photometer 5, a manometer 6, a valve 7, a suction pump 8, a valve 9, a manometer 10, a filter 11, a suction pump 12, a valve 13, an impactor 14 and a suction pump 15. The generator 2, the exposure room 3, the orofacial mask 4, the photometer 5, the manometers 6 and 10, the valves 7, 9 and 13, the filter 11 and the impactor 14 are housed inside a challenge room 16, while the air supplies 1' and 1" and the suction pumps 8, 12 and 15 are positioned outside this room 16.

The air supplies 1' and 1" are identical to the air supply 1 defined hereinbefore. They are each provided with a valve 7a. Alternatively, these valves 7a may belong to a same air supply system.

The generator of particles 2 is the one defined hereinbefore.

The exposure room 3 is further provided with the following particulars. The tube 150 rests on blocks 160 and is fastened to the blocks with straps 161.

The cover 152 is provided with a concentric bore in which is housed one end of a sleeve 180 (outer diameter: 1¼ in.). The opposite end of this sleeve 180 is connected with one end of an ABS pipe fitting 181 (diameter: 1κ in.) which is of the type provided, at one end thereof, with means adapted to fit and engage tightly the opposite end of the sleeve 180, and at the other end thereof, with means adapted to fit and engage one end of a "T" pipe fitting 230 made of brass. Each end of this fitting 230 is threaded. The end of the fitting 230 that engages the fitting 181 has a diameter larger than the other end of fitting 230 in order to minimize the possibility of backflow when the valve 9 is opened.

A pipe 231 having opposite threaded ends is screwed onto a threaded end of the fitting 230, the opposite end of this pipe 231 being screwed in a corresponding threaded bore of a valve 9 which is provided with opposite threaded bores.

A hose 232 is provided at each of its ends with threaded brass fittings 233 and 234. Fitting 233 is screwed with the remaining threaded bore of the valve 9. Fitting 234 is screwed with the remaining threaded bore of the valve 7a of the air supply 1".

A pipe 235 having opposite threaded ends is screwed with the inline threaded end of the fitting 230. The opposite end of this pipe 235 is screwed with one end of a "T" pipe fitting 240 made of brass. Each end of this fitting 240 is threaded.

A hose 241 having opposite end is provided with threaded brass fittings 242 and 243. Fitting 242 is screwed with one of the remaining threaded ends of the fitting 240. Fitting 243 is screwed with one end of a "T" pipe fitting 250 made of brass. Each end of this fitting 250 is threaded. Hose 241, illustrated in part, has a length of about 3 feet.

A pipe 255 having opposite threaded ends is screwed with one of the remaining threaded ends of the fitting 250. The opposite end of this pipe 255 is screwed with one end of a "T" pipe fitting 260 made of brass. Each end of this fitting 260 is threaded.

A pipe 265 having opposite threaded ends is screwed with one of the remaining threaded ends of the fitting 260. The opposite end of this pipe 265 is screwed with the outlet of the generator 2, which outlet is threaded.

A pipe 270 having opposite threaded ends is screwed with the remaining end of the fitting 260. The opposite end of this pipe 270 is screwed with the threaded inlet of a manometer 10 (This manometer is graded from 0 to 2 inches of water and has opposite inlets).

A plastic tube 275 having opposite ends is provided with threaded brass fittings 276 and 277. Fitting 276 is screwed with the remaining threaded inlet of manometer 10. Fitting 277 is screwed with the remaining threaded end of the fitting 240.

A pipe 280 having opposite threaded ends is screwed with the remaining end of fitting 250. The opposite end of pipe 280 is screwed with the threaded inlet 282 of a filter 11 of the type provided also with a hollow cylindrical room 283, a foam cylinder 284 and a threaded outlet 285.

A pipe 290 having opposite threaded ends is screwed with the outlet 285. The opposite end of pipe 290 is screwed in a corresponding threaded bore of a valve 13. This valve 13 is provided with opposite threaded bores.

A hose 300 is provided at each of its ends with threaded brass fittings 301 and 302. Fitting 301 is screwed with the remaining bore of the valve 13. Fitting 302 is screwed with the corresponding threaded brass fitting 303 of the suction pump 12.

The exposure room 3 is provided, at its mid-length, with four bores.

In a first bore, a sleeve 190 is housed. This sleeve 190 is of the type provided with two stoppers 191 and 192 (one on each side of the wall of the tube 150) and concentric protuberances 193. One end of a plastic hose 194 (e.g. a TYGONTM hose) is forced over the protuberances 193. The opposite end of this hose 194 is forced over the inlet of a manometer 6. This manometer (which is graded from 0.5 inch of water to 0.5 inch of water) is intended to measure the difference in pressure between the inside of the exposure room 3 and the atmospheric pressure.

In a second bore a sleeve 200 is housed. The junction between the sleeve 200 and the wall of the tube 150 is sealed with a layer of silicone 200a. One end of a plastic hose 201 is forced over one end of a sleeve 202 which is provided with protuberances 203 while the other end of this sleeve 202 is forced through a bore provided in a laboratory rubber cork 204. This cork 204 is of such a diameter that it can be forced in one end of the sleeve 200 to thus tightly connect the hose 201 with the sleeve 200. The opposite end of the hose 201 is forced over the inlet of a photometer 5 (e.g. a real-time aerosol monitor, model RAM-1 sold by GCA Environmental Instruments).

The photometer 5 is connected to an integrator 221 and to a strip chart recorder 220 which permit permits calibration and correlation of the results of the photometer to those of another sampling device (in this case the impactor). This photometer is provided with a double diaphragm pump to produce an input flow of 2 liters/minute.

In a third bore, one end of a sleeve 210 is housed. The junction between the sleeve 210 and the wall of the tube 150 is sealed with a layer 211 of silicone. In order to avoid the return of the breathed air to the exposure room, a one-way valve 212 is tightly forced in the sleeve 210 while its opposite end is tightly engaged by one end of a sleeve 213 whose opposite end is housed inside a bore provided in an orofacial mask 4. The one-way valve 212 is positioned so as to allow the aerosol contained in the tube 150 to flow toward the mask 4.

The mask 4 is also provided with another bore in which one end of a sleeve 214 having opposite ends is housed. This sleeve is equipped with a check valve in order to avoid expulsed air to be breathed again and has its opposite end connected with one end of a corrugated plastic tube 215. This kind of orofacial mask is commonly available and thereby does not need more elaborate description since it is well known to the skilled workman.

In a fourth bore, a sleeve 400 is housed. The unction between the sleeve 400 and the wall of the tube 150 is sealed with a layer of silicone 401. One end of the sleeve 400 is provided with a flat member 402 on which a cascade impactor 14 is mounted (in FIG. 4, the impactor is partly disconnected). This impactor SIERRA Model C290-MY, 34 mm dia. with silicone coating and is sold by Sierra Instruments Inc., Carmel Valley CA) has six stages. A gasket 403 is positioned between the flat member 402 and the base of the impactor 14 and then screws 404 are tightened with corresponding nuts 404'. The upper part of the impactor 14 is provided with a connecting sleeve 405 having protuberances 406.

A plastic tube 407, such as a TYGON TM hose having opposite ends, has one end forced over protuberances 406. The opposite end of this tube is forced over the inlet of the suction pump 15. This pump 15 is sold under the trademark GILLIAN HFS 113 ® and generates an inflow of 2 liters/minute.

The ends of sleeves 200, 210 and 400 which are positioned inside the room 3 are located at 4 cm from each other and are equidistant on the circumference of the tube 150.

Finally, the exposure room 3 is further provided with a foam disc 410. This foam collects particles of the aerosol (before the flow reaches the pump 8).

The device "DD" can be used as follows:
  the reservoir 81 is filled with a batch of specific particles of low diameter (e.g. $\leq 100$ μm and advantageously $\leq 15$ μm),
  the valve 7 is fully opened,
  suction pumps 8, 12 and 15 are started,
  the photometer 5, the graph recorder and the integrator are switched on,
  valves 7a are opened,
  the switch 54 is turned on and the dial 55 is set on a number selected between 0 and 11 (e.g. on the number 11). Vibrations are then communicated to the hopper 80.
  the needle valve 41 is adjusted so that pressure of about 2 kg/cm² can be read on the manometer 43 and a flow-rate of from 3 to 30 liters/minute can be read on the flow-meter 42.
  the valve 7 is slowly closed until the pressure read on the manometer is close to the atmospheric pressure and preferably slightly lower than the atmospheric pressure,
  the switch 56 is turned on the dial 57 is set on a number selected between 0 and 11 (e.g. on the number 3). Then the turntable is driven into a controlled axial rotation,
  the power supply 92 is switched on and the motor 83 is started so as to drive slowly the screw 82. The speed of the screw is controlled by variations of current and/or voltage applied to the electric motor,
  the concentration of particles in the aerosol is read on the photometer 5. (This concentration is determined from calibration curves which are plotted according to methods well known in the art). Then, if necessary, when the concentration of particles in the aerosol is either too high or too low with respect to the concentration at which a subject has to be challenged, any of the following steps may be considered.

When the concentration of particle is too low, the speed of the screw 82 may be increased so as more particles can be mixed with the air.

When the concentration of particles is too high, any of the following sequences of steps, or a combination of sequences can be carried out.

SEQUENCE 1

The valve 9 is slowly opened so as to dilute the flow of compressed aerosol. The pressure is read on the manometer 10 so as to prevent the aerosol from refluxing in the generator 2, and valve 7 is slightly opened until the pressure read on, and the manometer is close to the atmospheric pressure and preferably slightly lower than the atmospheric pressure. Then the concentration is read on the photometer 5 or recorder 220 and if the concentration is still too high, the above steps are repeated.

SEQUENCE 2

The valve 13 is slightly opened in order to divide the flow of compressed aerosol. Then the valve 7 is slowly closed until the pressure read on the manometer 6 is close to the atmospheric pressure. Then the concentration is read on the photometer 5 or recorder 220 and if is still too high, the above steps are repeated.

SEQUENCE 3

The speed of rotation of the screw 82 is lowered, the concentration is read on the photometer 5 or recorder 220, and if the concentration is still too high, the above steps are repeated.

Finally, when the appropriate concentration of particles has been reached, a subject covers the natural apertures of his respiratory system with the mask 4 and inhales at least one time a part of the aerosol flowing in the exposure room 3 while the particle content of this aerosol is measured by the photometer 5 and recorded on the recorder 220. The size of particles of the aerosol is determined by the impactor 14, and then the reaction of the subject to the aerosol is noted. If the subject has to inhale more than one time, he expires through the valve and the tubing 214, and then inhales again....

To stop the device "DD", the power supply 92 is turned off, valves 7a and eventually 7 (if desired), 9 and 13 are closed, the photometer, the integrator and the recorder are switched off, suction pumps 8, 12 and 15 are turned off, switches 54 and 56 are turned off and the impactor 14 is removed for usual quantitative analysis purposes.

EXAMPLES

Specific inhalation challenges were carried out with the device shown in FIGS. 2 to 6, on 20 subjects suspected of having occupational asthma. For each challenge, the above mentioned procedure was carried out under the following operational data, the reservoir 81 was filled with a batch of specific powder product with particles of low diameter (e.g. $\leq 15$ μm, preferably $\leq 10$ μm) (Specific products were ground with a CYCLONE SAMPLE MILL, UD Corporation, Boulder Co.).

the dial 55 was set on the number 11, the valve 7 was positioned until the pressure read on the manometer became slightly lower than the atmospheric pressure, the dial 57 was set on the number 3.

The appropriate concentration of particles was generally set close to or below 10 mg/$m^3$. This is the accepted upper level for short term exposure (TLV-STEL) to soft wood dusts. The TLV-STEL has not been determined for the other powder of this example.

A subject covered the natural apertures of his respiratory system with the mask 4 and inhaled at least one time a part of the aerosol flowing in the exposure room 3 (under a flow of about 20 to 40 liters/ minute, preferably under a flow of about 25 liters/minute which is near the average flow of air that is normally breathed by a subject). a conventional flow meter could be mounted through hose 300 and/or hose 232 and/or hose **7*b* and/or hose 164**. However, this is not essential.

Simultaneously, the particle content of the aerosol was measured by the photometer 5 and recorded on the graph recorder 220, and the percentage of inhaled particles, according to their size, is determined by weighing the filters of the cascade impactor 14. (However, when the size of particles poured into the reservoir 81 is known, a cascade impactor is not necessary).

The photometer 5 assessed the surface area of particles, but not the mass. The factor to transform the surface area into mass therefore was obtained for each product by weighing the total in the cascade impactor during the procedure. Factors were calculated in duplicate by running the device with the relevant dust for periods varying from 30 to 90 minutes (until a total exposure of 1000 mg/$m^3$ has been reached); the mean of two reproducible (± 1) values was kept for analysis. Information on the diameter of particles was obtained at the same time.

In this example, a ventilatory scan was performed on one control subject (non smoker, non asthmatic) by marking control wood dust with technicium $^{99}$. Technicium$^{99}$ was selected for its short half-life. The wood dust was sifted and mixed in a 30% (volume/volume) isopropylalcohol-physiologic saline solution to which the technicium$^{99}$ was added. The dust was then dried at 140° C. for 15 minutes. A postero-anterior view lung scan was performed after the tagged wood dust had been inhaled with the device of FIG. 2 for 30 minutes at concentrations of 5 mg/$m^3$ according to the photometer reading.

SUBJECTS

Twenty subjects suspected of having occupational asthma were included in these examples. All had answered questionnaires suggesting work-related asthmatic symptomatology that improved away from the work environment.

SKIN TESTING

Skin tests were performed using the prick method with a battery of 15 common inhalant allergens. In the case of flour, extra tests were done with individual cereals (wheat, oat, barley, corn, rye) provided by Hollister-stier Lab., Rexdale, Ont. Subjects exposed to guar gum were also tested with the substance diluted to a concentration of 1 mg/ml.

SPECIFIC INHALATION CHALLENGES WITH THE DEVICE ACCORDING TO THE INVENTION

Spirometry was carried out on a control day according to the standards of the American Thoracic Society (American Thoracic Society, Standardization of Spirometry. 1987 update, An. Rev. Respir. Dis. 1987, 136:1285–98). Subjects were first exposed to a control dust: lactose in the case of flour, psyllium, guar gum, formaldehyde, and a wood dust of local species (black spruce, Balsam fir, Jack pine) in the case of Western red cedar. Duration of exposure was 15 minutes. After exposure, FEV 1 (forced expiratory volume in one second ) was reassessed every 10 minutes for one hour, every 30 minutes for one hour and then every hour for a total of 8 hours of post-exposure monitoring. Maximum within-day variations in FEV 1 had to be ≦10% for the tests to be continued.

Bronchial responsiveness was assessed at the end of the day with histamine or methacholine using the standardized procedure outlined by Cockcroft and coworkers (Cockcroft DW, Killian DN, Mellon JJA, Hargreave FE. Bronchial reactivity to inhaled histamine: a method and clinical survey, Clin Allergy 1977; 7:235–43) and a Wright's nebulizer (output = 0.14 ml/min) at tidal volume breathing for 2 minutes. On the following day, after assessing baseline spirometry (baseline FEV 1 had to be ±10% from one day to the next), subjects were exposed to the suspected agent in a progressive manner, generally one breath, 5–10 sec, 15 sec, 30 sec, 1 min, 2 min, 5 min, etc. Spirometry was assessed immediately and 10 minutes after each exposure until a decrease of 20% occurred in those cases where immediate bronchoconstriction was suspected, i.e., in which subjects had positive skin reactions to flour, psyllium or guar gum. For these individuals, the tests were completed that day. For the other suspected agents for which skin testing was not performed because the information is not relevant (Western red cedar, formaldehyde), the maximum duration of exposure increased from day to day, from 1 to 5, 30 and finally 120 minutes. Bronchial responsiveness was reassessed at the end of the last day of the challenge or the following morning. For those who did not experience significant bronchoconstriction, the challenge was performed using the traditional method by asking the subject to tip the relevant dust from one tray to another in a challenge room on the same day or the following day.

ANALYSIS OF RESULTS

Reference values for spirometry were obtained from Knudson and coworkers (Knudson RD, Lebowitz MD, Holberg CJ, Burrows B. Changes in the normal maximal expiratory flow-volume curve with growth and aging. Am Rev Respir Dis 1983; 127:725–34). The provocative concentration of histamine/methacholine causing a 20% fall in FEV 1 (PC 20) was interpolated from individual dose-response curves drawn on a semi-logarithmic non-cumulative scale. Significant bronchial hyperresponsiveness was set at a PC 20 value ≦16 mg/ml (Malo JL, Pineau L, Cartier A, Martin RR. Reference values of the provocative concentrations of methacholine that cause 6% and 20% changes in forced expiratory volume in one second in a normal population. Am Rev Respir Dis 1983; 128:8-11). Changes in PC 20 ≧ 3.2-fold difference from one day to the next were considered to be significant (Dehaut P, Rachiele A, Martin RR, Malo JL., Histamine dose-response curves in asthma; reproducibility and sensitivity of different indices to asses response. Thorax 1983; 38:516-22).

RESULTS

FIGS. 7a to 7c illustrate the concentration of particles in the traditional exposure as measured by the photometer located close to the mouth (approximately 10 cm), for three different products (flour, guar gum and Western red cedar). Large variations in the concentration of particles were encountered with the tipping process. By comparison, FIG. 8a to 8c shows the stability of the concentration of particles for the same agents using the device according to the invention as measured by the photometer 5. The ventilatory lung scan of the control subject using the control wood dust indicates that the tagged inhaled particles reached the lung bases.

Twenty subjects underwent specific inhalation challenges. There were 13 men and 7 women whose mean age was 40 years (range = 24-61 yrs). Atopy was present in 16 subjects. All subjects who had immediate skin reactions to flour, guar gum and psyllium also had positive inhalation challenges, with one exception (no. 19) who had an immediate skin reaction to psyllium and a PC 20 of 2.1 mg/ml. The mean duration of symptoms was 5 years (range = 1-20 yrs). Mean baseline FEV 1 was 98% pred (range = 73-117% pred); only one subject had a value <80% pred. The mean geometric PC 20 result was 1.4 mg/ml (range = 0.15-90 mg/ml). All subjects with one exception had significant bronchial hyperresponsiveness as defined by a PC 20 < 16 mg/ml.

Figure 9A:
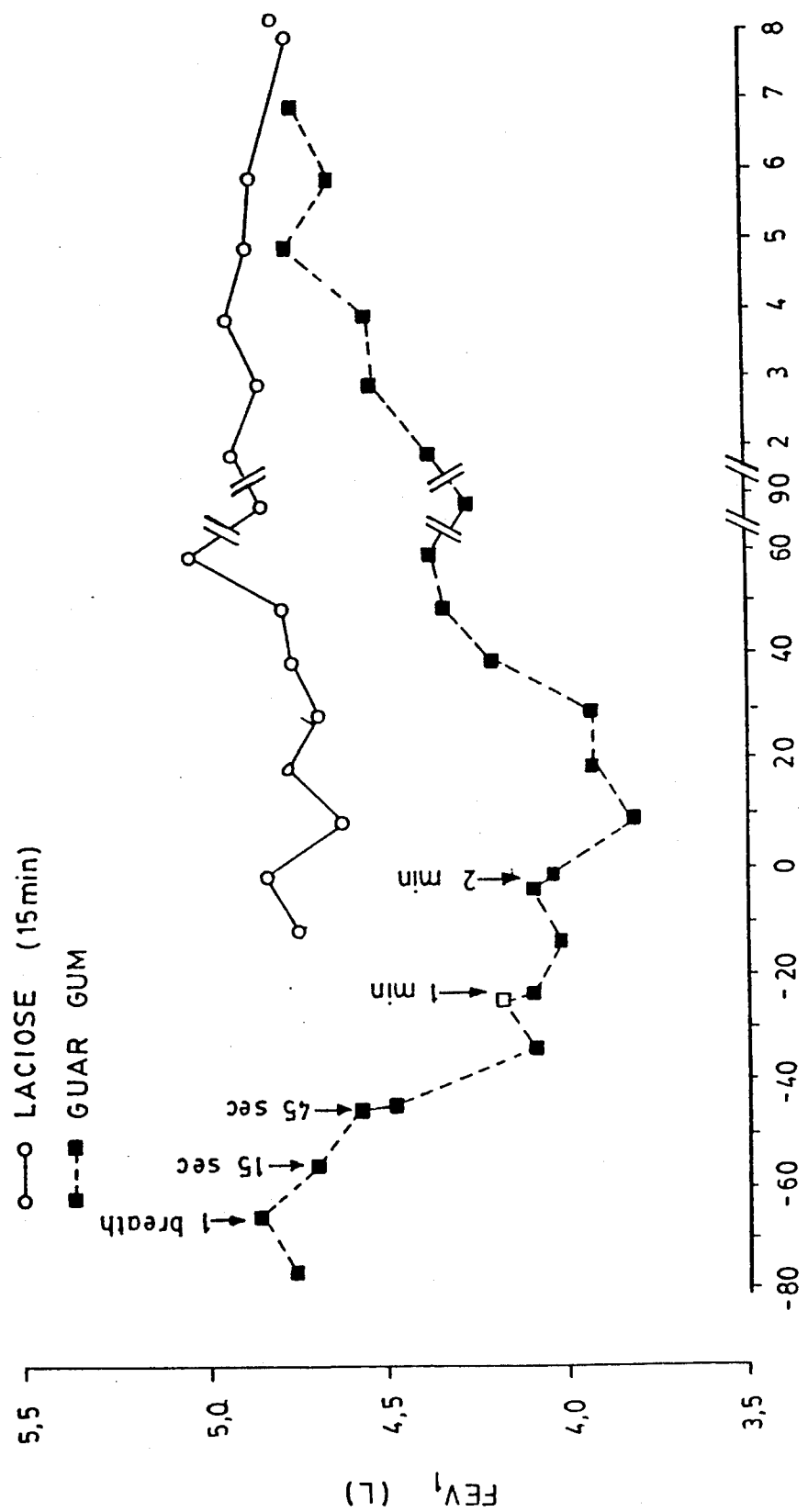
FIGS. 9a and 9b are examples of dose-response curves in two subjects with guar gum (top panel) and flour (lower panel). The decreases in FEV 1 are progressive. "O" time corresponds to the end of last exposure showing the consecutive durations of exposure.
Figure 9B:
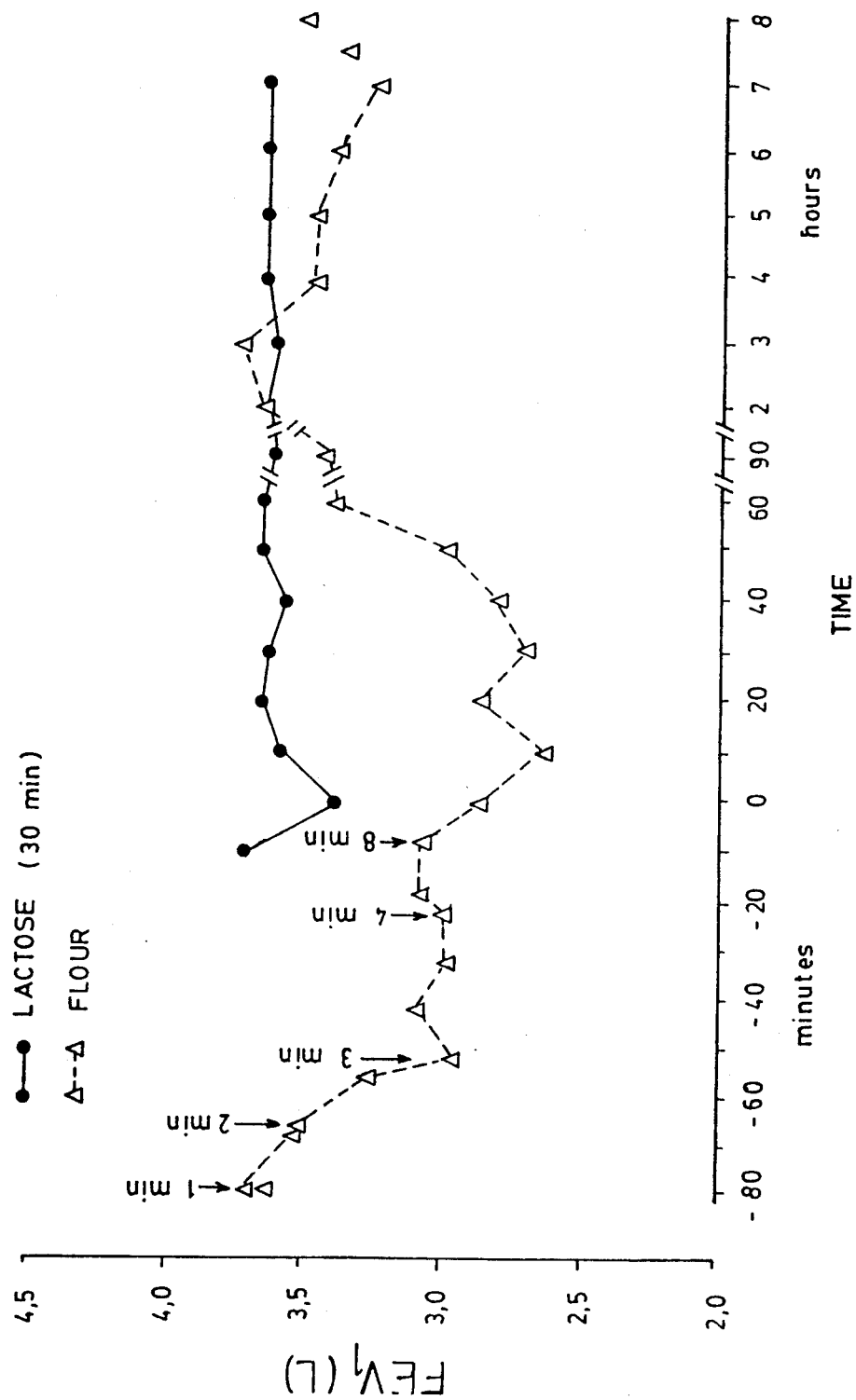

Table 1 outlines exposure and reactions. Psyllium was the most common occupational agent (n=7), followed by flour (n−6), guar gum (n=3), Western red cedar (n=3) and formaldehyde resin (n=1). The duration of exposure was variable, from one breath to a maximum of 120 minutes. Six were documented. The five subjects who showed no reactions significant changes in FEV 1 underwent realistic exposure in which they were asked to tip the relevant powder in the traditional way. No significant changes in FEV 1 or PC 20 were documented. For subjects nos. 4 and 9, the exposure was relatively short with the device according to the invention as they showed no skin reactivity to psyllium. It was previously shown that occupational asthma to psyllium is IgE mediated. In the case of positive tests, maximum decreases in FEV 1 varied from 19 to 42% at the time of maximum reaction, either immediate, late or dual. With the immediate and dual reactions, the percentage decreases in FEV 1 varied from 12 to 40% (mean=24%) 10 minutes after exposure, and from 15 to 42% (mean=24%) 20 minutes after exposure. FIG. 9a and 9b shows examples of dose-response curves obtained with a device according to the invention for guar gum and flour. It can be seen that immediate reactions were progressive.

Correcting factors were obtained to determine the relationship between the mass of particles measured by the photometer and their actual weight, and are listed in Table 2. When the factors were being calculated, information on the diameter of the particles was also obtained. Thirty to 87% of inhaled particles had a diameter ≧10 $\mu$.

DISCUSSION

This study shows that the use of a device according to the invention has several advantages over traditional realistic exposure. First, as shown in FIGS. 8a to 8c, the concentration of particles can be kept relatively constant throughout the exposure, unlike the realistic approach where tipping dust results in highly variable concentrations, as illustrated in FIGS. 7a to 7c.

Secondly, concentrations of particles can be maintained near or below TLV-STEL (threshold limit valueshort term exposure level) which has been determined to be safe in the case of soft wood dusts (American Conference of Governmental Industrial Hygienists. TLVs. Threshold limit values and biological exposure indices for 1986-87. Cincinnati: ACGIH, 1987). These concentrations are not thought to cause irritation of the skin although their effect on the bronchial mucosa is unknown. Exposing individuals with heightened bronchial responsiveness to concentrations of soft wood dusts greater than TLV-STEL can cause changes in spirometry in a minority of subjects 1 per 12 subjects tested). Maintaining the concentration of particles at a relatively low level is important for several reasons, particularly in distinguishing irritant from specific ("sensitizing") reactions. The latter are generally identified as occupational asthma, whereas the former, which are likely to occur in individuals with the most pronounced bronchial hyperresponsiveness, can generally be prevented by the use of inhaled beta-2 adrenergic agents and may not necessarily require withdrawal from work. It can be difficult to distinguish between the two types of reactions from a functional point of view. Bronchial reactions that occur after the inhalation of occupational or normal allergens ((Pepys J, Hutchcroft BJ. Bronchial provocation tests in etiologic diagnosis and analysis of asthma. Am Rev Respir Dis 1975; 112:829-59) (Malo JL, Cartier A, L'Archeveque J, Ghezzo H, Martin RR. Kinetics of the recovery from bronchial obstruction due to hyperventilation of cold air in asthmatic subjects. Eur Respir J 1988; 1:384-8)) and non-specific agents ((hyperventilation of unconditioned air) (Cartier A, Thomson NC, Frith PA, Roberts R, Hargreave FE. Allergen-induced increase in bronchial responsiveness to histamine; relationship to the late asthmatic response and change in airway caliber. J Allergy Clin Immunol 1982; 70:170-7)) usually peak in 5 to 20 minutes, and recovery is general within 30 to 60 minutes. Exposing the individual to low concentrations of dust can therefore prevent the occurrence of non-specific reactions.

Thirdly, information on the diameter of particles is significant. Indeed, knowing dusts which are respirable (diameters ≦10 $\mu$) is relevent, as higher diameter dusts are generally retained in the upper airways.

The device according to the invention is also easy to handle and clean. The exposure room 3, made of plexiglass, can be washed, dried, and used for a different powder on the same day.

Finally, information on the concentration of particles can be obtained minute to minute by reading the photometer. If the correcting factor is obtained before hand the mass can be deduced from the reading. Particles can also be prepared before hand, grinding them in such a way that their granulometric properties are known. The amount of respirable dusts can then be obtained.

TABLE 1

Exposure and reactions

| No. | Agent | Duration of exposure (min) | Type of reaction | Maximum fall in FEV 1* | Concentration of particles on photometer (mg/m$^3$) | Realistic exposure |
|---|---|---|---|---|---|---|
| 1 | red cedar | 40 | late | 22 | 5 | ND |
| 2 | guar gum | 4.5 | immediate | 21 | 1.5 | ND |
| 3 | flour | 70 | dual | 20 | 0.5 | ND |
| 4 | psyllium | 8.5 | absent | not significant | 0.5 | done (15 min, negative) |
| 5 | guar gum | 2.5 | immediate | 29 | 0.8 | ND |
| 6 | flour | 1 breath | immediate | 21 | 1.5 | ND |
| 7 | flour | 125 | absent | not significant | 1.0 | done (21 min, negative) |
| 8 | psyllium | 1.2 | dual | 31 | 0.2 | ND |
| 9 | psyllium | 18.5 | absent | not significant | 0.2 | done (18.5 min, negative) |
| 10 | flour | 30 | immediate | 32 | 5 | ND |
| 11 | psyllium | 2.5 | dual | 19 | 0.2 | ND |
| 12 | red cedar | 5 | late | 30 | 5 | ND |
| 13 | psyllium | 1.5 | dual | 32 | 0.6 | ND |
| 14 | red cedar | 36 | late | 21 | 5 | ND |
| 15 | formaldehyde resin | 120 | absent | not significant | 5 | done (51 min, negative) |
| 16 | flour | 19 | immediate | 28 | 3 | ND |
| 17 | guar gum | 0.5 | immediate | 22 | 1 | ND |
| 18 | psyllium | 21 | dual | 42 | 1 | ND |
| 19 | psyllium | 36 | absent | not significant | 1 | done (32 min, negative) |
| 20 | flour | 5 | dual | 28 | 3 | ND |

Legend: *At the time of immediate or late reactions. ND = not done: realistic exposure asking subjects to tip powder from one tray to another was only carried out with those subjects whose inhalation challenges were negative with the device according to the invention.

TABLE 2

Correcting factors and diameter of particles

| Occupational agent | Correcting factor* | % of particles $\leq 10\mu$ |
|---|---|---|
| lactose | 3.5 | 48 |
| control wood dust | 1.8 | 61 |
| flour | 4.2 | 30 |
| psyllium | 3.1 | 44 |
| guar gum | 4.5 | 69 |
| Western red cedar | 2.7 | 58 |
| formaldehyde resin | 1.6 | 87 |

Legend: *The correcting factor is the amount by which the value of the concentration of particles as read by the photometer (see Table 1) must be multiplied in order to transform density (which the photometer measures) into mass. These factors were obtained by comparing the densities from the photometer for periods varying from 30 to 90 min with the weight of the filters in the cascade impactor. The mean value of two reproducible ($\pm 1$) readings was kept. The percentage of particles was also reproducible for the two readings ($\pm 10\%$).

I claim:

1. Apparatus for specific inhalation challenges, comprising:

aerosol generation means for continuously suspending in a flow of compressed air a predetermined amount of specific particles to thus generate a compressed aerosol of predetermined composition, said aerosol generation means comprising an inlet connected to a supply of compressed air by a tube, means connected to a supply of specific particles for continuously and uniformly mixing a part of said particles with the compressed air, and means defining a compressed aerosol outlet;

pressure adjustment means for adjusting the pressure of the compressed aerosol to a pressure close to atmospheric pressure, said pressure adjustment means comprising:

a suction pump including at least one suction pump inlet, a manometer including at least one manometer inlet, an exposure room comprising a duct having at least one lateral wall and opposite ends, each end being closed by a cover, said room further comprising:

an exposure room inlet positioned in one of said covers, said exposure room inlet including aerosol inlet means for permitting fluid communication between the exposure room and said compressed aerosol outlet, a first exposure room outlet positioned in the other of said covers and including first fluid communication means for permitting fluid communication between the exposure room and said suction pump inlet, said first fluid communication means comprising suction pump adjustment means including a valve for permitting adjustment of a draft of said suction pump, a second exposure room outlet positioned in said lateral wall and including second fluid communication means for permitting fluid communication between the exposure room and said manometer inlet, a third exposure room outlet positioned in said lateral wall, and a fourth exposure room outlet positioned in said lateral wall;

said apparatus further comprising mask means including an orofacial mask for covering natural apertures of the respiratory system of a subject, said mask means including means for permitting fluid communication between the mask and said third exposure room outlet;

a particle content measuring device including means for permitting fluid communication between an inlet of said device and said fourth exposure room outlet, said device also including means for continuously drawing a small part of the aerosol flowing in the room and measuring its particle content.

2. Apparatus as claimed in claim 1, wherein said aerosol generation means comprises a particle generator having an inlet, defining the inlet of the aerosol generation means connected to the supply of compressed air, an outlet, which is part of said means defining the compressed aerosol outlet of the aerosol generation means, and said means connected to said supply of specific particles for continuously and uniformly mixing a part of said particles with the compressed air comprising:

a base including at least one post, a platform mounted on the post and positioned above the base, a conveyor comprising a turntable pivotably mounted on said base and means including an electric motor for driving said turntable into a controlled axial rotation, said supply of compressed air including an air ejector mounted on the platform, a hopper mounted on the platform, and a vibrator mounted on the platform;

wherein said air ejector comprises said inlet which is connected to the supply of compressed air, an air ejector outlet, an air ejector outlet tube comprising a first end and an opposite end, said first end being connected with the air ejector outlet, means including the opposite end of said air ejector outlet tube for defining said outlet which is part of said means defining the compressed aerosol outlet of the aerosol generation means, an opening positioned between the air ejector outlet and inlet, an air ejector pipe comprising a first end and an opposite end, said first end being connected with the opening, means including the opposite end of said pipe for defining a suction post such that compressed air flowing through said ejector creates a vacuum in the air ejector pipe;

wherein said hopper comprises a reservoir containing a predetermined amount of specific particles and having a reservoir top, a reservoir bottom, reservoir lateral walls that converge towards each other from the reservoir top towards the reservoir bottom, an opening in one of said reservoir lateral walls in the vicinity of the reservoir bottom, an endless screw passing through said opening and being at least partly in contact with said particles, and means for driving said screw in order to continuously and uniformly discharge particles through said opening in one of said reservoir lateral walls;

wherein said turntable includes a disk having a top surface and a concentric axis of rotation, said conveyor also including a groove provided in the top surface and concentric with its axis of rotation, said groove having a smooth bottom and smooth lateral walls that diverge from each other from the bottom of said groove to the top surface of the disk, said turntable being rotationally mounted on said base in such a way that distinct segments of the groove are respectively positioned under the opening in one of the reservoir lateral walls and the means for defining a suction post; and wherein said vibrator comprises an electromechanical device which includes means for communicating vibrations to the reservoir of the hopper in order to continuously bring the particles contained in the reservoir towards the reservoir bottom and thus allow full contact between at least a part of said screw and the particles.

3. Apparatus as claimed in claim 2, wherein said means for driving said screw comprises an electric stepping motor.

4. Apparatus as claimed in claim 2, wherein said means for communicating vibrations to the reservoir includes means for providing said vibrations at a frequency of approximately 50 Hertz.

5. Apparatus as claimed in claim 1, wherein the exposure room comprises a tube and said lateral wall includes a cylindrical surface, said covers being of such a diameter that they fit against respective ends of said tube, said exposure room further comprising an O-ring seal having a diameter such that the O-ring seal can be positioned between an end of the tube and one of said covers, and fastening means for holding one of said covers against an end of the tube, thereby collapsing the O-ring seal., said exposure room inlet being defined by a first connecting sleeve passing through and integral with said one of said covers, said sleeve being connected to said aerosol generation means by an aerosol-to-exposure room connection tube having opposite ends and which is part of said aerosol inlet means, one end of said connection tube being connected to the first connecting sleeve while the opposite end of said tube is connected to the outlet of the aerosol generation means, said first outlet being defined by a second connecting sleeve passing through and integral with the other of said covers, said second connecting sleeve being connected to said suction pump inlet by said adjustment means, a tube included in said first fluid communication means, said tube having opposite ends, and said tube being provided with said valve and having one end thereof connected to the second connecting sleeve while the opposite end of said tube is connected to the suction pump inlet, said second outlet being defined by a third connecting sleeve passing through and integral with said cylindrical surface, said third connecting sleeve being connected with of said manometer inlet by a tube included in said second fluid communication means, said tube having opposite ends, one end thereof being connected to the third connecting sleeve while the opposite end of said tube is connected to said manometer inlet, and said third and fourth outlets being defined by respective fourth and fifth connecting sleeves passing through and integral with said cylindrical surface, said fourth connecting sleeve being connected with means including a sixth connecting sleeve for defining an orofacial mask inlet and being part of said means for permitting fluid communication between the mask and the third exposure room outlet, and said fifth connecting sleeve being connected by a tube included in said means for permitting fluid communication between an inlet of said device and said fourth outlet, said tube having opposite ends, one end thereof being connected to the fifth connecting sleeve while the opposite end of said tube is connected with means including a seventh connecting sleeve for defining said inlet of the measuring device.

6. Apparatus as claimed in claim 5, wherein said sixth connecting sleeve includes a unidirectional valve, and wherein said mask means is further provided with a second mask outlet defined by an eighth connecting sleeve, one end of said eighth connecting sleeve being integral with said mask means while another end of said eighth connecting sleeve is connected with one end of a tube located at a position distant form the subject.

7. Apparatus as claimed in claim 5, wherein said connection tube positioned between the exposure room inlet and the aerosol generation means comprises:
a first fitting having three openings, two of said openings of said first fitting being connected respectively to the first connecting sleeve and to one end of the aerosol-to-exposure room connection tube, while the third opening of said first fitting is connected to another compressed air supply by another tube having opposite ends and a valve, one end of said another tube being connected to said another compressed air supply while the opposite end of said another tube is connected to the third opening of said first fitting, and said opening of said first fitting which is connected to the first connecting sleeve having a diameter larger than a diameter of any of the other openings of said first fitting;
a second fitting and a third fitting, each provided with three respective openings, two of said respective openings being connected through a first segment of said aerosol-to-exposure room connection tube that is positioned between the compressed aerosol outlet and the first fitting and respective third openings being connected with inlets of another manometer, said another manometer having two distinct inlets; and
a fourth fitting having three openings, two of said fourth fitting openings being connected through a segment of said first segment of said aerosol-to-exposure room connection tube positioned between said second and third fittings, the third opening of said fourth fitting being connected to a suction pump inlet of a second suction pump by a second suction pump inlet tube having opposite ends and a valve, one end of said second suction pump inlet tube being connected via a second suction pump inlet pipe to the third opening of the fourth fitting while the opposite end of said second suction pump inlet tube is connected to said suction pump inlet of the second suction pump.

8. A device as claimed in claim 7, further comprising a filter which includes a foam disc positioned inside the second suction pump inlet pipe.

9. Apparatus as claimed in claim 5, wherein a disc of foam is positioned inside said exposure room between the first exposure room outlet and the other exposure room outlets.

10. Apparatus as claimed in claim 1, wherein said measuring device is a photometer.

11. Apparatus as claimed in claim 10, wherein said photometer is connected to at least one of the following devices: a digital reader, a graphic recorder, or an integrator.

12. Apparatus as claimed in claim 1, further comprising size measuring means for measuring the size of particles of the aerosol and a fifth outlet in the lateral wall of the exposure room, said fifth outlet being defined by a connecting sleeve passing through and integral with said lateral wall, said fifth outlet being positioned close to the third and fourth outlets, and said sleeve of the fifth outlet being connected with an inlet of said size measuring means.

13. Apparatus as claimed in claim 12, wherein said size measuring means includes a cascade impactor.

14. Apparatus as claimed in claim 12, wherein said third, fourth, and fifth outlets of said exposure room are positioned in a single plane at angles of 120° from each other, said plane being perpendicular to a longitudinal axis of the exposure room, said exposure room forming a tube.

15. Apparatus as claimed in claim 12, wherein a disc of foam is positioned inside said exposure room between the first exposure room outlet and the other exposure room outlets.

16. A method for carrying out specific inhalation challenges, comparing the steps of:
continuously suspending in a flow of compressed air a predetermined amount of specific particles to thus generate a compressed aerosol of predetermined composition;
supplying said aerosol to an exposure room;
adjusting the pressure of the compressed aerosol to a pressure close to atmospheric pressure;
covering the natural apertures of the respiratory system of a subject with an orofacial masks, and placing the orofacial mask in fluid communication with the exposure room;
placing a particle content measuring device in fluid communication with said exposure room and continuously drawing a small part of the aerosol flowing into the room in order to measure its particle content.

17. A method for carrying out specific inhalation challenges, comprising the steps of:
opening a valve positioned between a first suction pump and a first outlet of an exposure room;
starting the first suction pump, a second and a third suction pump, and a device intended to continuously draw part of an aerosol flowing in an exposure room in order to measure a particle content of the aerosol flowing in the exposure room;
establishing a flow of compressed air through a particle generator which includes a turntable, a vibrator, and a screw;
starting the vibrator to cause particles to contact the screw, starting the screw to convey them to the turntable, and driving the turntable into a constant speed of rotation to bring the particles to an air ejector which mixes the particles in the flow of compressed air;
partly closing the valve positioned between the first suction pump and the first outlet of the exposure room until the pressure read on a first manometer is set close to atmospheric pressure;
reading the concentration of particles in the aerosol on a photometer which is part of the said device, and, if the particle content of the aerosol is excessive, performing one of the following two steps: (1) partly opening a valve positioned between a second supply of compressed air and an opening of the exposure room to dilute the aerosol and subsequently checking on a second manometer whether or not the aerosol is flowing in the appropriate direction, and (2) partly opening a valve positioned between the third suction pump and another opening of the exposure room in order to divide the aerosol and subsequently adjusting the valve position between the first suction pump and the first outlet of the room to the pressure read on the first manometer;

repeating the reading step until the concentration read on the photometer corresponds to the one at which a subject has to be challenged; and covering natural apertures of the respiratory system of a subject with an orofacial mask and having the subject breathe at least one time a part of the aerosol that is flowing in the exposure room while the photometer is continuously and simultaneously measuring the particle content of the aerosol and a cascade impactor is determining the particle size of the aerosol.

18. A method as claimed in claim 17, wherein the pressure inside the exposure room is always set slightly lower than atmospheric pressure.

19. A method as claimed in claim 18, wherein each of the suction pumps having at least one outlet that is connected to the outside of the room, and wherein an outlet of a tube connected to the orofacial mask is also connected with the outside of the room, said method further comprising the steps of causing exhaust air to be evacuated outside of the room.

20. A method as claimed in claim 17, further comprising the step of timing the challenge by a chronometer.

21. Apparatus for specific inhalation challenges, comprising:

aerosol generation means for continuously suspending in a flow of compressed air a predetermined amount of specific particles to thus generate a compressed aerosol of predetermined composition;

pressure adjustment means including an exposure room for adjusting a pressure of the compressed aerosol to a pressure close to atmospheric pressure;

mask means including an orofacial mask for covering natural aperture of the respiratory system of a subject;

means for permitting fluid communication between said mask and said exposure room;

means for permitting fluid communication between said aerosol generation means and said exposure room;

measuring means for drawing a part of the aerosol flowing in the room and measuring its particle content.

* * * * *